(12) United States Patent
Brown et al.

(10) Patent No.: US 9,533,023 B2
(45) Date of Patent: Jan. 3, 2017

(54) EIF4E BINDING PEPTIDES

(71) Applicant: Agency for Science, Technology and Research, Singapore (SG)

(72) Inventors: Christopher John Brown, Singapore (SG); Cheng San Brian Chia, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/675,675

(22) Filed: Mar. 31, 2015

(65) Prior Publication Data

US 2016/0038567 A1 Feb. 11, 2016

Related U.S. Application Data

(62) Division of application No. 13/695,011, filed as application No. PCT/SG2011/000165 on Apr. 27, 2011, now Pat. No. 9,018,348.

(60) Provisional application No. 61/328,437, filed on Apr. 27, 2010.

(51) Int. Cl.
- A61K 38/00 (2006.01)
- C07K 7/08 (2006.01)
- A61K 38/17 (2006.01)
- C07K 14/47 (2006.01)

(52) U.S. Cl.
CPC ............ *A61K 38/1709* (2013.01); *C07K 7/08* (2013.01); *C07K 14/4705* (2013.01); *A61K 38/00* (2013.01); *C07K 2319/10* (2013.01)

(58) Field of Classification Search
None
See application file for complete search history.

(56) References Cited

U.S. PATENT DOCUMENTS

| | | | |
|---|---|---|---|
| 5,428,128 A | 6/1995 | Mensi-Fattohi et al. | |
| 5,612,460 A | 3/1997 | Zalipsky | |
| 5,643,575 A | 7/1997 | Martinez et al. | |
| 5,880,131 A | 3/1999 | Greenwald et al. | |
| 6,127,355 A | 10/2000 | Greenwald et al. | |
| 6,380,161 B1 | 4/2002 | Williams et al. | |
| 7,425,544 B2 * | 9/2008 | Dobie .................... | C07H 21/00 435/375 |

FOREIGN PATENT DOCUMENTS

| | | |
|---|---|---|
| EP | 0 401 384 A1 | 12/1990 |
| WO | WO 00/78803 A2 | 12/2000 |
| WO | WO 00/78803 A3 | 12/2000 |
| WO | WO 03/057235 A2 | 7/2003 |
| WO | WO 2004/047871 A2 | 6/2004 |

OTHER PUBLICATIONS

Neves-Pereira et al (J Met Genet 46: 759-765, 2009).*
PCT International Search Report for PCT Application No. PCT/SG2011/000165, 4 pgs., (Aug. 4, 2011).
PCT Written Opinion of the International Searching Authority for PCT Application No. PCT/SG2011/000165, 6 pgs., (Aug. 4, 2011).
PCT Notification concerning Transmittal of International Preliminary Report on Patentability (Chapter I of the Patent Cooperation Treaty) for PCT Application No. PCT/SG2011/000165, 8 pgs., (Nov. 8, 2012).
Stephen Fawell, et al., "Tat-Mediated Delivery of Heterologous Proteins into Cells", Proc. Natl. Acad. Sci. USA, vol. 91, pp. 664-668, (Jan. 1994).
James P. Tam, "Synthetic Peptide Vaccine Design: Synthesis and Properties of a High-Density Multiple Antigenic Peptide System", Proc. Natl. Acad. Sci. USA, vol. 85, pp. 5409-5413, (Aug. 1988).
IUPAC-IUB Joint Commission on Biochemical Nomenclature (JCBN), "Nomenclature and Symbolism for Amino Acids and Peptides—Recommendations 1983", Eur. J. of Biochem., vol. 138, pp. 9-37, (1984).
Joseph Marcotrigiano, et al., "Cap-Dependent Translation Initiation in Eukaryotes is Regulated by a Molecular Mimic of eIF4G", Molecular Cell, vol. 3, pp. 707-716, (Jun. 1999).
Christopher J. Brown, et al., "Crystallization of eIF4E Complexed with eIF4GI Peptide and Glycerol Reveals Distinct Structural Differences around the Cap-Binding Site", Cell Cycle, vol. 8, No. 12, pp. 1905-1911, (Jun. 15, 2009).
Song Yi Ko, et al., "Inhibition of Ovarian Cancer Growth by a Tumor-Targeting Peptide that Binds Eukaryotic Translation Initiation Factor 4E", Clin. Cancer Res., vol. 15, No. 13, pp. 4336-4347, (Jul. 1, 2009).
Arrigo De Benedetti, et al., "eIF-4E Expression and its Role in Malignancies and Metastases", Oncogene, vol. 23, pp. 3189-3199, (2004).
David A. Case, et al., "The Amber Biomolecular Simulation Programs", J. Comput. Chem., vol. 26, No. 16, pp. 1668-1688, (Dec. 2005).
Junmei Wang, et al., "Automatic Atom Type and Bond Type Perception in Molecular Mechanical Calculations", Journal of Molecular Graphics and Modelling, vol. 25, pp. 247-260, (2006).
M. Scott Shell, et al., "A Test on Peptide Stability of Amber Force Fields with Implicit Solvation", J. Phys. Chem. B., vol. 112, No. 22, pp. 6878-6886, (Jun. 5, 2008).
Alexey Onufriev, et al., "Exploring Protein Native States and Large-Scale Conformational Changes With a Modified Generalized Born Model", Proteins: Structure, Function, and Bioinformatics, vol. 55, pp. 383-394, (2004).
William Humphrey, et al., "VMD: Visual Molecular Dynamics", Journal of Molecular Graphics, vol. 14, pp. 33-38, (1996).
Sylvie Mader, et al., "The Translation Initiation Factor eIF-4E Binds to a Common Motif Shared by the Translation Factor eIF-4g and the Translational Repressors 4E-Binding Proteins", Molecular and Cellular Biology, vol. 15, No. 9, pp. 4990-4997, (Sep. 1995).
Terence P. Herbert, et al., "Rapid Induction of Apoptosis Mediated by Peptides that Bind Initiation Factor eIF4E", Current Biology, vol. 10, pp. 793-796, (2000).
Nathan J. Moerke, et al., "Small-Molecule Inhibition of the Interaction between the Translation Initiation Factors eIF4E and eIF4G", Cell, vol. 128, pp. 257-267, (Jan. 26, 2007).

(Continued)

*Primary Examiner* — Gregory S Emch
*Assistant Examiner* — Aditi Dutt
(74) *Attorney, Agent, or Firm* — Blakely, Sokoloff, Taylor & Zafman LLP

(57) ABSTRACT

The present invention relates to modified eIF4G1 peptides, uses thereof and pharmaceutical compositions comprising the modified eIF4G1 peptides.

5 Claims, 26 Drawing Sheets

(56) References Cited

OTHER PUBLICATIONS

Christopher J. Brown, et al., "Stabilizing the eIF4G1 α-helix Increases its Binding Affinity with eIF4E: Implications for Peptidomimetic Design Strategies", J. Mol Biol., vol. 405, pp. 736-753, (2011).

W. F. Van Gunsteren, et al., "Algorithms for Macromolecular Dynamics and Constraint Dynamics," Molecular Physics, vol. 34, No. 5, pp. 1311-1327, (1977).

Mei-Chu Lo, et al., "Evaluation of Fluorescence-Based Thermal Shift Assays for Hit Identification in Drug Discovery," Analytical Biochemistry, vol. 332, No. 1, pp. 153-159, (Sep. 1, 2004).

Christopher J. Brown, et al., "Crystallographic and Mass Spectrometric Characterisation of eIF4E with $N^7$-Alkylated Cap Derivatives," J. Mol. Biol., vol. 372, No. 1, pp. 7-15, (2007).

John A. Cook, et al., "Viability Measurements in Mammalian Cell Systems," Analytical Biochemistry, vol. 179, No. 1, pp. 1-7, (May 15, 1989).

European Patent Office Communication enclosing Extended European Search Report for European Patent Application No. 11775390.5-1401, 8 pgs., (Nov. 18, 2013).

C. Toniolo, et al., "Effect of Phenyl Ring Position in the $C^\alpha$-Methylated α-Amino Acid Side Chain on Peptide Preferred Conformation", Biopolymers, vol. 40, pp. 523-527, (1996).

Andrew J. Doig, et al., "N- and C-capping Preferences for All 20 Amino Acids in α-Helical Peptides", Protein Science, vol. 4, No. 7, pp. 1325-1336, (Jul. 1995).

Beate Koksch, et al., "Fluoro-Modified Chemotactic Peptides: fMLF Analogues", Journal of Peptide Science, vol. 10, pp. 67-81, (2004).

Meital Reches, et al., "Designed Aromatic Homo-Dipeptides: Formation of Ordered Nanostructures and Potential Nanotechnological Applications", Physical Biology, vol. 3, No. 1, pp. S10-S19, (2006).

Bill Eldridge, et al., "An In Vitro Selection Strategy for Conferring Protease Resistance to Ligand Binding Peptides", Protein Engineering, Design & Selection, vol. 22, No. 11, pp. 691-698, (2009).

\* cited by examiner

```
                                            624   629   634
                                             |     |     |
eIF4G1                              KKRYDREFLLGFQF-NH2
Tr1                                 KKRYDREFLL-NH2
Tr2                                    YDREFLLGFQF-NH2
Tr3                                    YDREFLLGFQ-NH2
Control                                ADREFLLGFQF-NH2
Tr2_AIB1                               YXREFLLGFQF-NH2
Tr2_AIB2                               YDRXFLLGFQF-NH2
Tr2_AIB3                               YDREFLLXFQF-NH2
Tr2_AIB4                               YDREFLLGFXF-NH2
Tr2_AIB3_ALA                           YDREFLLAFQF-NH2
Tr2_AIB3_A3C                           YDREFLL3FQF-NH2
Tr2_AIB3_A4C                           YDREFLL4FQF-NH2
Tr2_AIB3_A5C                           YDREFLL5FQF-NH2
Tr2_ALA_A5C1                           YAREFLL5FQF-NH2
Tr2_ALA_A5C2                           YDAEFLL5FQF-NH2
Tr2_ALA_A5C3                           YDRAFLL5FQF-NH2
Tr2_ALA_A5C4                           YDREALL5FQF-NH2
Tr2_ALA_A5C5                           YDREFLL5AQF-NH2
Tr2_ALA_A5C6                           YDREFLL5FAF-NH2
Tr2_ALA_A5C7                           YDREFLL5FQA-NH2
Tr2_me5_1                              YDRE*LL5FQF-NH2
Tr2_me5_2                              YDREFLL5*QF-NH2
Tr2_me5_3                              YDREFLL5FQ*-NH2
eIF4G1_me5                          KKRYDRE*LL5FQF-NH2
TAT                        YGRKKRRQRRR-NH2
TAT_eIF4G1                 YGRKKRRQRRRGTKKRYDREFLLGFQF-NH2
TAT_eIF4G1_Cntrl           YGRKKRRQRRRGTKKRADREFAAGFQF-NH2
TAT_eIF4G1_me5             YGRKKRRQRRRGTKKRYDRE*LL5FQF-NH2
TAT_eIF4G1_me5_Cntrl       YGRKKRRQRRRGTKKRADRE*AA5FQF-NH2
GT_eI4FG1                              GTKKRYDREFLLGFQF-NH2
GT_eI4FG1_Cntrl                        GTKKRADREFAAGFQF-NH2
GT_eIF4G1_me5                          GTKKRYDRE*LL5FQF-NH2
GT_eIF4G1_me5_Cntrl                    GTKKRADRE*AA5FQF-NH2
Conserved Motif                        YXXXXLΦ
```

FIG. 1B

| Minimal Motif | ΔT (°C) | Estimated K_d (nM) |
|---|---|---|
| eIF4G1 | 8.7 | 470 |
| Tr1 | 1.7* | 50160 |
| Tr2 | 4.2 | 5960 |
| Tr3 | 2.25* | 35210 |
| Control | 0.65* | n/a |
| AIB scan for sites of helix stabilization | | |
| Tr2_AIB1 | 1.32 | 29840 |
| Tr2_AIB2 | - | n/a |
| Tr2_AIB3 | 5.42 | 3050 |
| Tr2_AIB4 | 1.52 | 25080 |
| Replacement of Glycine by ALA and amino-cycloalkane-1-carboxylic acid derivatives | | |
| Tr2_AIB3_ALA | 5.60 | 2550 |
| Tr2_AIB3_A3C | 5.67 | 2500 |
| Tr2_AIB3_A4C | 5.80 | 2350 |
| Tr2_AIB3_A5C | 6.60 | 1450 |
| Alanine scan of A5C substituted eIF4GI peptide. | | |
| Tr2_Ala_A5C1 | 5.02 | 760 |
| Tr2_Ala_A5C2 | 2.69 | 14300 |
| Tr2_Ala_A5C3 | 4.22 | 1220 |
| Tr2_Ala_A5C4 | 3.72 | 8090 |
| Tr2_Ala_A5C5 | 3.65 | 8400 |
| Tr2_Ala_A5C6 | 6.72 | 1370 |
| Tr2_Ala_A5C7 | 5.48 | 2900 |
| CA methlylation of Phe residue 628 dramatically increases the Affinity of Derivative Peptide | | |
| Tr2_me5_1 | 8.8 | 360 |
| Tr2_me5_2 | NA | n/a |
| Tr2_me5_3 | 5.8 | 2400 |
| Re-addition of the N-terminal to Residues 624-634 generates a High Affinity eIF4GI peptide derivative | | |
| eIF4G1_me5 | 14.6 | 7 |

FIG. 2

| Peptides | $K_d$ (nM) | $\Delta H$ (kCal mol$^{-1}$K$^{-1}$) | $-T\Delta S$ (kCal mol$^{-1}$K$^{-1}$) |
|---|---|---|---|
| Tr2 | 1014.20±65.83 | -10.95±0.13 | -2.91 |
| Tr2_me5_1 | 145.99±22.81 | -16.07±0.2 | -6.89 |
| eIF4G1 | 147.93±22.81 | -9.7±0.05 | -0.58 |
| eIF4G1_me5 | 9.43±2.57 | -14.45±0.11 | -3.69 |

FIG. 3A

Tr2_me5_1 eIF4G1_me5

Tr2 eIF4G1

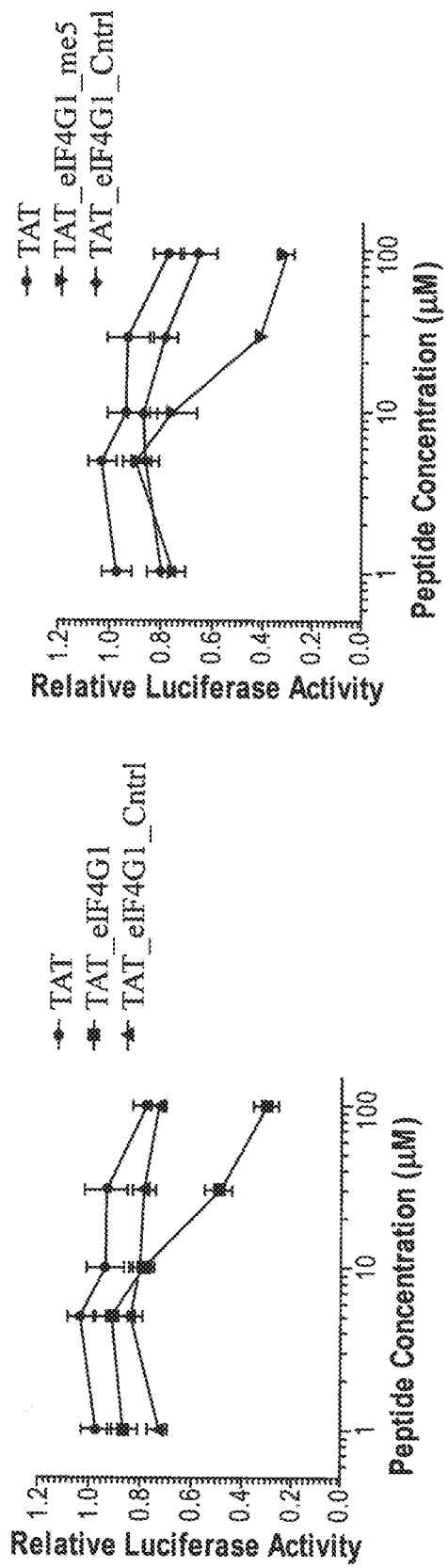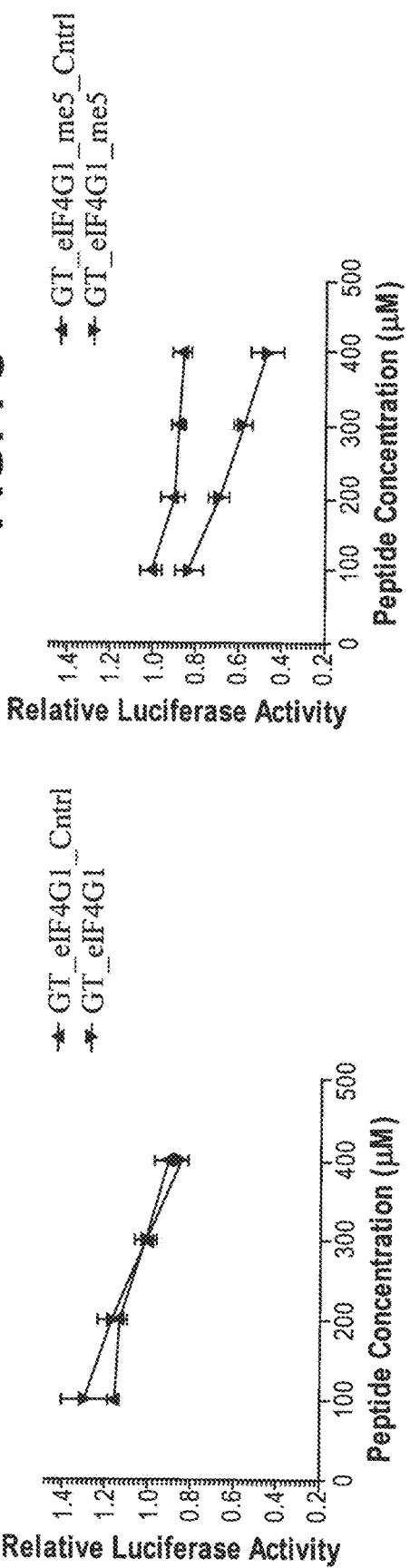

| | DMSO 0.1% | GT_eIF4G1_me5 (400μM) | GT_eIF4G1_me5_Cntrl (400μM) |
|---|---|---|---|
| G1 (%) | 50.5±2.6 | 47.5±0.9 (p=0.5493) | 46.1±2.6 (p=0.3156) |
| S (%) | 8.2±0.9 | 2.2±0.1 (p=0.0065) | 9.0+0.8 (p=0.4466) |
| G2 (%) | 19.8±0.4 | 16.9±1.1 (p=0.0606) | 27.2±3.6 (p=0.1034) |
| Sub G1 (%) | 15.6±5.2 | 25.9±2.0 (p=0.0261) | 11.1±2.8 (p=0.3967) |

FIG. 9

|  | TAT | PBS Mock |
|---|---|---|
| G1 (%) | 40.1±0.6 (p=0.0013) | 35.3±0.8 |
| S (%) | 16.8±1.12 (p=0.2077) | 15.5±1.1 |
| G2 (%) | 13.3±1.3 (p=0.0017) | 21.4±1.4 |
| Sub G1 (%) | 24.0±0.9 (p=0.1402) | 21.8±1.9 |
|  | TAT_eIF4G1 | TAT_eIF4G1_Cntrl |
| G1 (%) | 34.7±2.8 (p=0.1793) | 38.6±3.0 |
| S (%) | 5.5±0.2 (p<0.0001) | 15.2±1.0 |
| G2 (%) | 5.5±0.4 (p=0.0002) | 24.8±2.6 |
| Sub G1 (%) | 43.4±3.2 (p<0.0001) | 15.2±1.0 |
|  | TAT_eIF4G1_me5 | TAT_eIF4G1_me5_Cntrl |
| G1 (%) | 17.0±0.7 (p<0.0001) | 28.5±0.1 |
| S (%) | 2.6±0.3 (p<0.0001) | 9.1±0.2 |
| G2 (%) | 3.2±0.1 (p<0.0001) | 15.6±0.3 |
| Sub G1 (%) | 71.7±1.0 (p<0.0001) | 40.1±0.8 |

FIG. 10

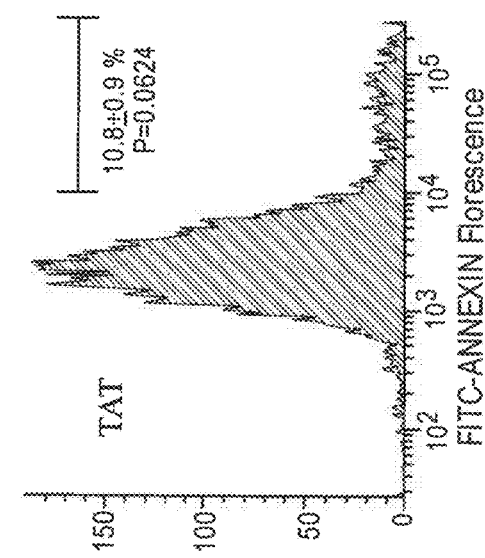
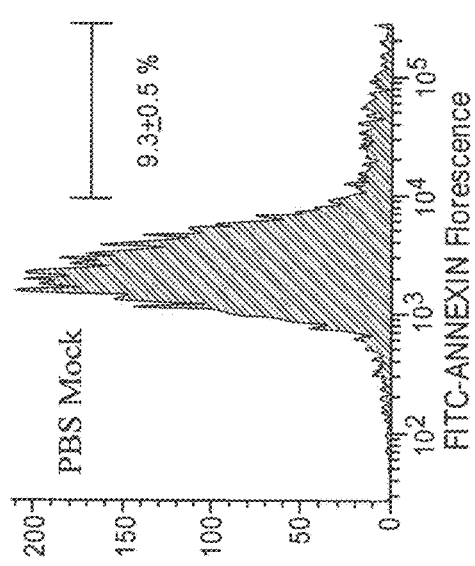
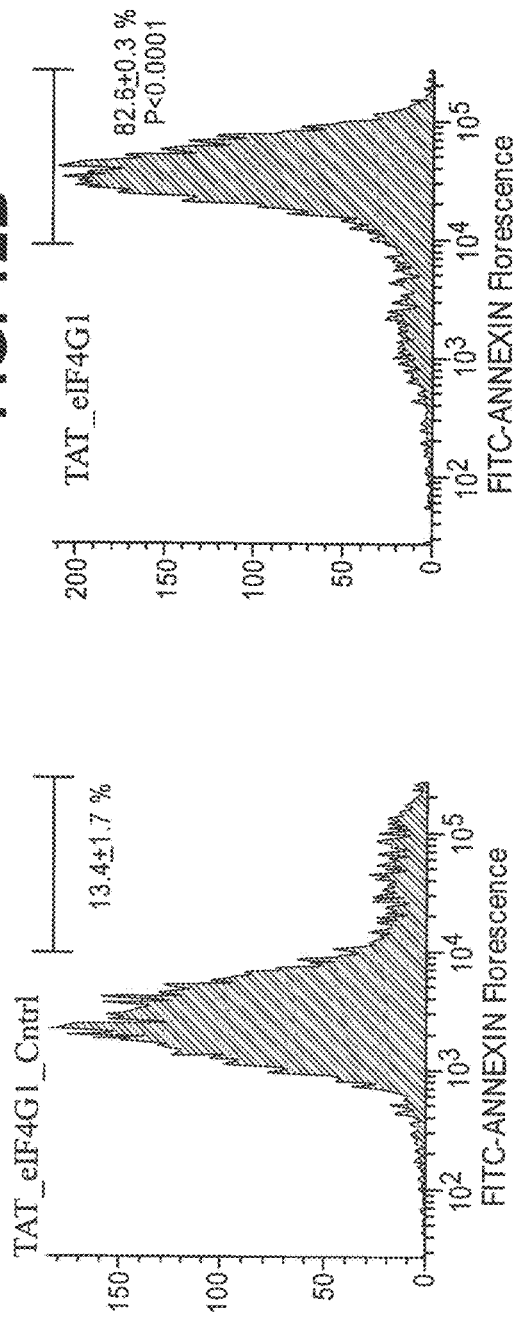

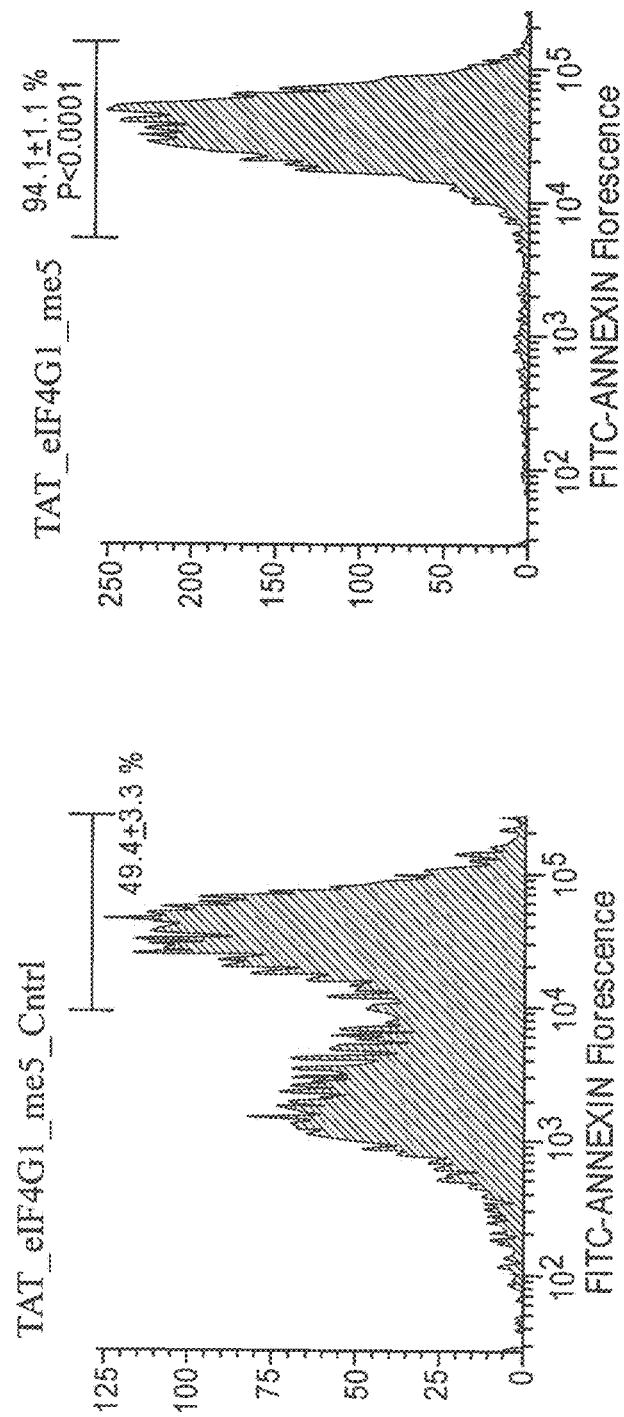

| Peptides | $K_d$ (nM) | $\Delta H$ (kCal mol$^{-1}$K$^{-1}$) | $\Delta S$ (Cal mol$^{-1}$K$^{-1}$) |
|---|---|---|---|
| TAT-eIF4GI | 56.18±2.55 | -5.52±0.06 | 15 |
| TAT_eIF4GI_me5 | 10.17±8.60 | -12.39±0.10 | -5.69 |

FIG. 13A

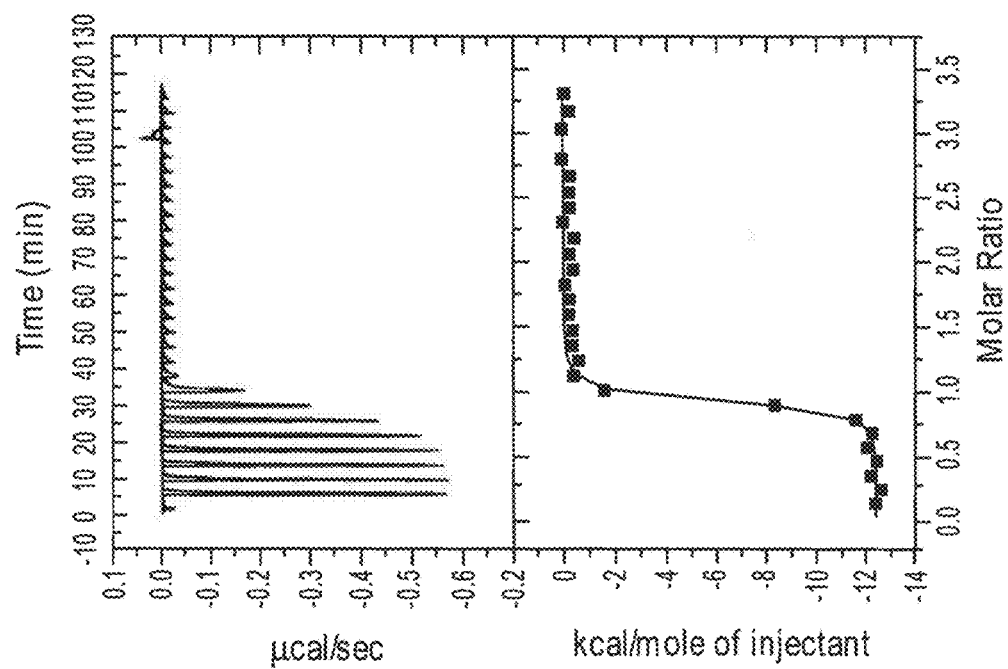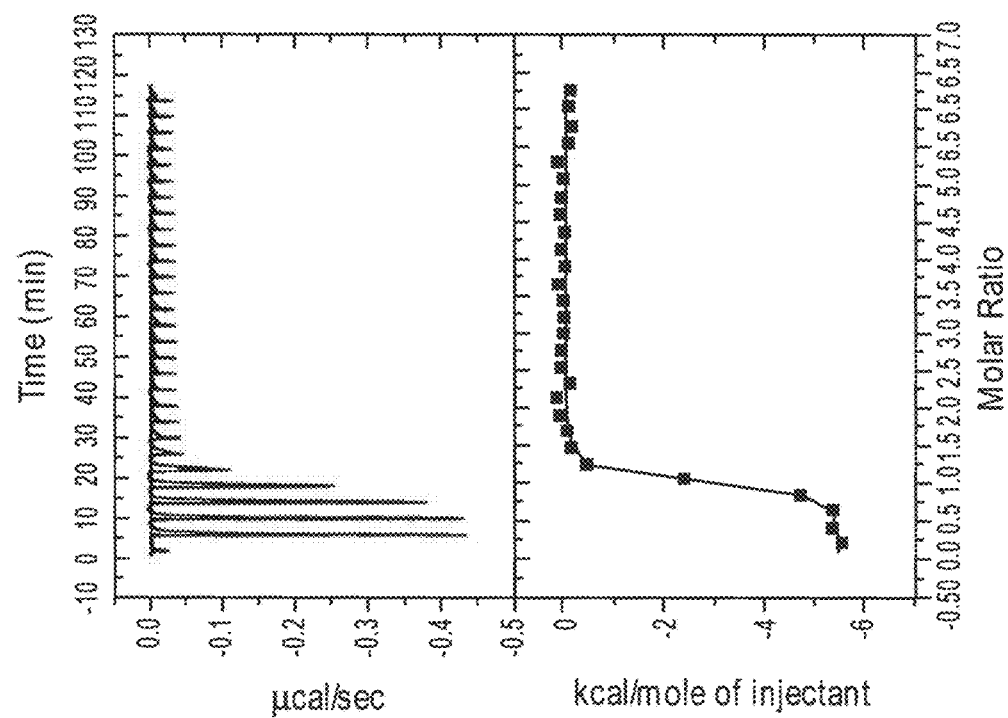
FIG. 13B

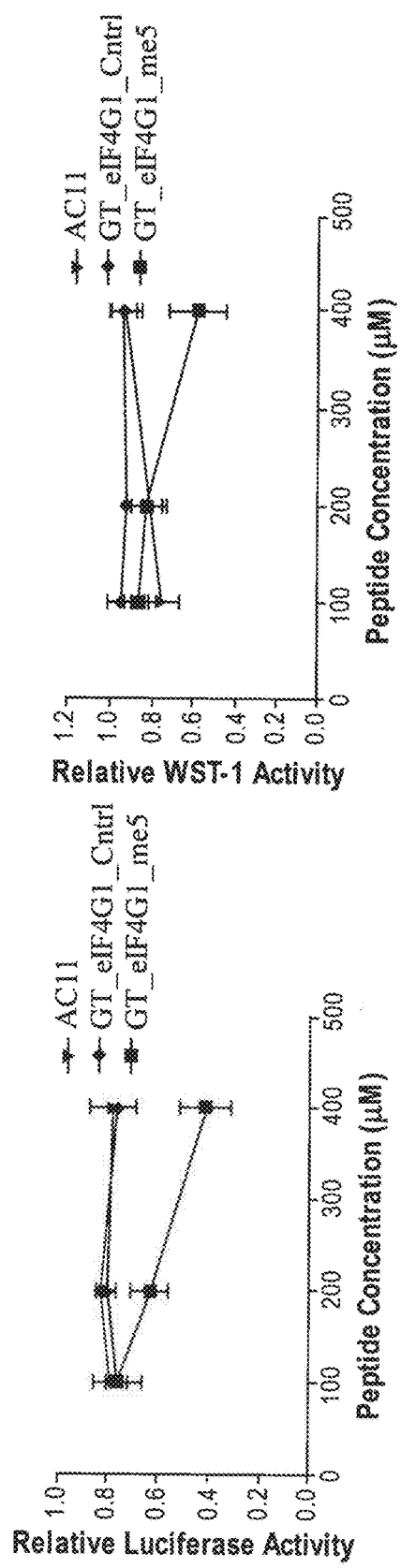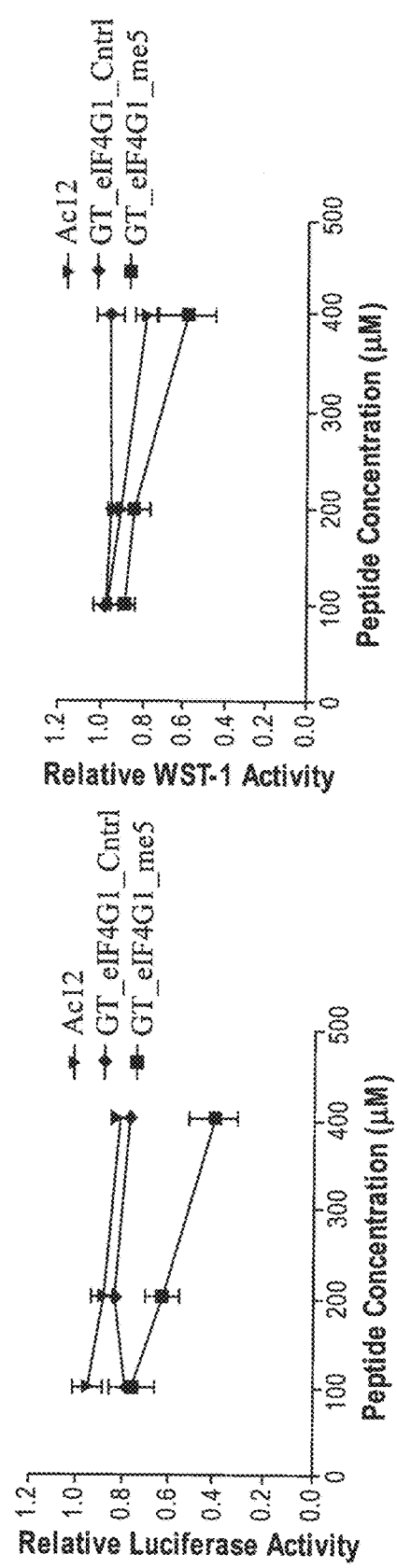
FIG. 15A
FIG. 15B

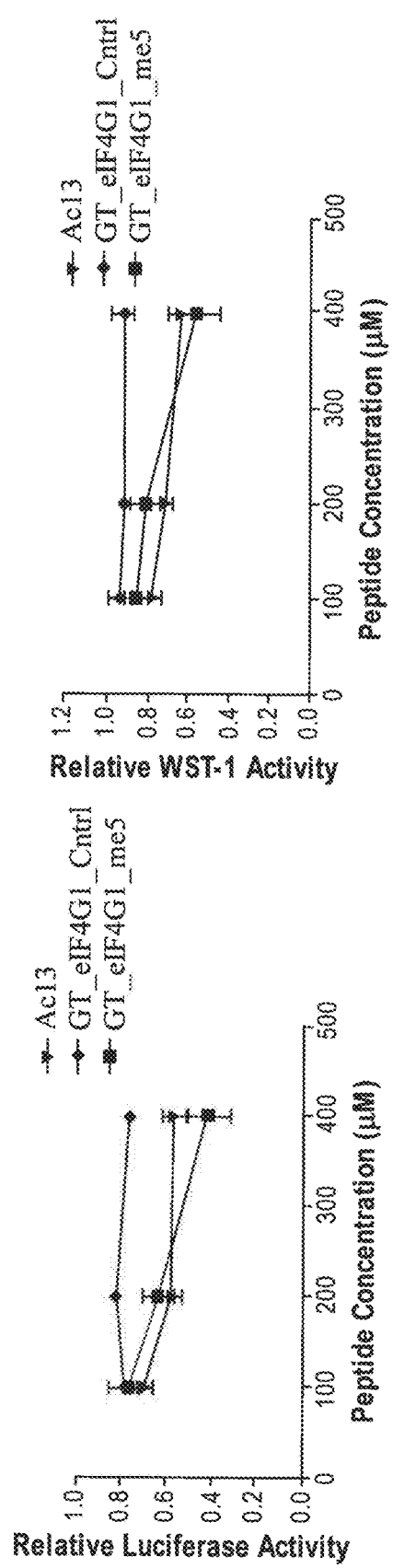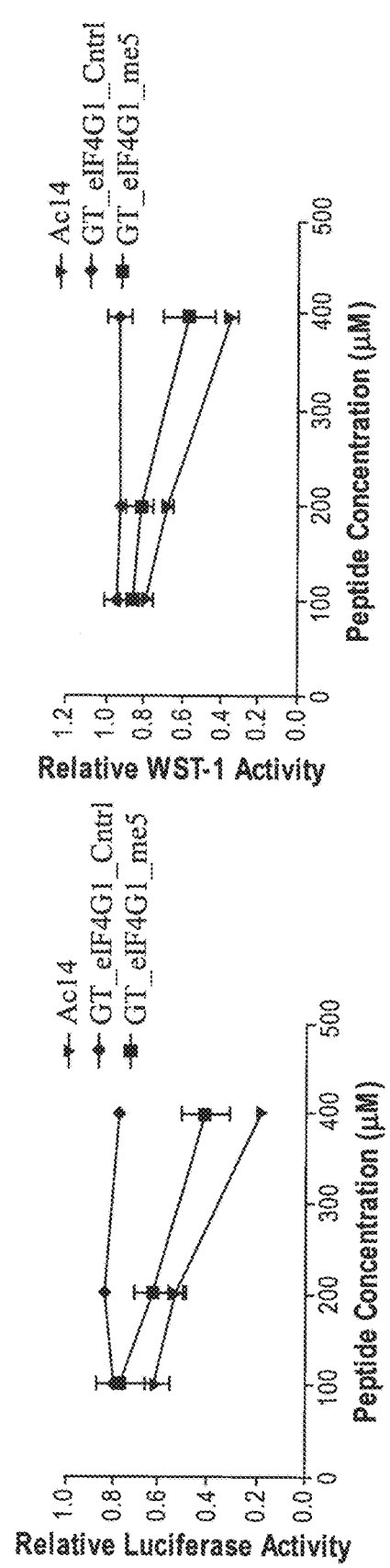
FIG. 15C
FIG. 15D

NH2-G-T-K-K-R-Y-D-R-E-*-L-L-5-F-Q-F-NH2 GT_eIF4G1_me5
NH2-G-T-K-K-R-A-D-R-E-*-A-A-5-F-Q-F-NH2 GT_eIF4G1_Cntrl
Ac-G-T-K-K-R-Y-D-R-E-*-L-L-5-F-Q-F-NH2 Ac16
Ac-T-K-K-R-Y-D-R-E-*-L-L-5-F-Q-F-NH2 Ac15
Ac-K-K-R-Y-D-R-E-*-L-L-5-F-Q-F-NH2 Ac14
Ac-K-R-Y-D-R-E-*-L-L-5-F-Q-F-NH2 Ac13
Ac-R-Y-D-R-E-*-L-L-5-F-Q-F-NH2 Ac12
Ac-Y-D-R-E-*-L-L-5-F-Q-F-NH2 Ac11

* = C-alpha Methyl phenylalnine
5=Aminocyclopentanoic acid

FIG. 15G

EIF4E BINDING PEPTIDES

CROSS-REFERENCE TO RELATED APPLICATION

This application is a divisional of U.S. patent application Ser. No. 13/695,011, having a 371(c) date of Feb. 5, 2013, which is a U.S. National Phase Application under 35 U.S.C. 371 of International Application No. PCT/SG2011/000165, filed Apr. 27, 2011, entitled "EIF4E BINDING PEPTIDES," which claims the benefit of priority of U.S. provisional application No. 61/328,437, filed Apr. 27, 2010, the contents of which were incorporated by reference in their entirety for all purposes.

INCORPORATION BY REFERENCE

This application incorporates by reference the material (i.e., Sequence Listing) in the ASCII text file named Sequence_listing_ST25.txt, created Oct. 25, 2012 (modified Oct. 23, 2012), having a file size of 16,869 bytes.

FIELD OF THE INVENTION

The present invention lies in the field of molecular biology and relates to modified eIF4G1 peptides and pharmaceutical uses thereof.

BACKGROUND OF THE INVENTION

In multiple human cancers, the function of the eukaryotic translation initiation factor 4E (eIF4E) is elevated and directly related to disease progression. eIF4E binds the 7-methylguanosine cap at the 5' end of cellular mRNAs, delivering the mRNA to the eIF4F complex to enable ribosome loading and eventual protein translation. The eIF4F complex is comprised of the scaffolding protein eIF4G, the ATP-dependent helicase eIF4A and eIF4E. Once loaded onto the 5' end of an mRNA, the eIF4F complex is thought to scan 5'-3', unwinding secondary structure in the mRNA 5' untranslated region (UTR) to reveal the initiation codon for ribosome loading.

The majority of cellular mRNAs (e.g., β-actin) contain a relatively short and unstructured (limited C+G content) 5' UTR, through which the eIF4F complex can easily scan to reveal the translation initiation codon. These "strong" mRNAs are therefore efficiently translated, even when eIF4F is limiting. Conversely, "weak" mRNAs (e.g., VEGF, c-myc) have longer 5' UTR sequences with multiple open reading frames and complex hairpin secondary structures that encumber efficient scanning and require greater energy expenditure to unravel. These mRNAs are thereby inefficiently translated except under conditions of elevated eIF4F activity, as in cancer. In addition, recent work has now shown that eIF4E can mediate the enhanced nucleocytoplasmic transport of select "weak" mRNAs involved in cell growth, including cyclin D. In cancer, eIF4F activity is elevated either by increased eIF4E expression or by enhanced signaling through the ras/PI3K/AKT/TOR axis or both. This consequently enables a disproportionate increase in the translation of these weak mRNAs, many of which are involved in cell growth (cyclin D1), cell survival (survivin, Bcl-2, Mcl-1) or angiogenesis (VEGF, FGF-2).

eIF4E was first defined as a proto-oncogene after its over-expression induced cellular transformation and tumorigenesis in mouse fibroblasts. Subsequently, inhibition of eIF4E expression by ectopic expression of antisense RNA or 4EBP1 was shown to suppress not only tumor formation but also tumor invasiveness and metastasis. Analyses of many different tumor types have now revealed that eIF4E expression is elevated in lymphomas as well as cancers of the breast, lung, head and neck, esophagus, skin, bladder, colon, cervix and prostate. Invariably, such over-expression has been related to disease progression and poorer patient survival. Inhibition of eIF4E is therefore an attractive target for anti-cancer therapeutics and also interestingly a potentially target for treatment of autism as well. Here linkage of autism to the EIF4E region on chromosome 4q has been found in genome wide linkage studies.

A recent report has indicated that the small molecule ribavirin might interfere with the eIF4E:cap interaction and may therefore present a clinical opportunity as an eIF4E-targeted therapy. As anticipated, ribavirin treatment selectively diminished the expression of key, eIF4E-dependent proteins such as cyclin D1 and suppressed tumor growth. However, whether or not ribavirin actually binds eIF4E is controversial. Consequently, a more directed approach to develop small molecule inhibitors of the eIF4E:7-methylguanosine cap interaction might be a fruitful approach for the development of an eIF4E-specific small molecule therapy. To date, no such drug-like inhibitors of the eIF4E-cap interaction have been reported.

An alternative approach to targeting the eIF4E-cap interaction is to selectively disrupt the interaction of eIF4E with eIF4G, thereby disabling the formation of the eIF4F complex. An alternative approach to targeting eIF4E would be to reduce eIF4E protein expression using antisense oligonucloetides (ASOs). eIF4E ASOs have been shown to effectively reduce both eIF4E RNA and protein in a wide array of transfected human and murine cells, subsequently reducing the expression of the malignancy-related proteins-specifically cyclin D1, VEGF, c-myc, survivin and BCL-2. Importantly, ASO mediated reduction of eIF4E did not affect the expression of β-actin, a protein encoded by a "strong" mRNA nor did it reduce overall protein synthesis substantially.

It is therefore an object of the present invention to provide a eIF4E binding peptide that can be efficiently used for the treatment or prevention of cancer and autism.

SUMMARY OF THE INVENTION

In one aspect, the invention provides a modified eIF4G1 peptide, wherein the peptide has been modified to stabilize the α-helix.

In another aspect, the invention provides a pharmaceutical composition comprising a modified eIF4G1 peptide as defined herein.

In a further aspect, the invention provides a nucleic acid encoding a peptide as defined herein.

In yet another aspect, the invention provides a vector comprising a nucleic acid as defined herein.

In yet a further aspect, the invention provides a method of inhibiting eIF4E. The method includes administering a pharmaceutically effective amount of a modified eIF4G1 peptide as defined herein.

In another aspect, the invention provides a method for the treatment of autism and cancer. The method includes administering a pharmaceutically effective amount of a modified eIF4G1 peptide as defined herein or a pharmaceutical composition as defined herein.

BRIEF DESCRIPTION OF THE DRAWINGS

The invention will be better understood with reference to the detailed description when considered in conjunction with the non-limiting examples and the accompanying drawings, in which:

FIG. 1B shows the peptide key and alignment of the peptides and modified peptides described herein in the iterative design of a helically stabilized peptide against eIF4E. X=Amino isobutyric acid (Aib), 3=1-amino cyclopropanoic acid, 4=1-amino cyclobutanoic acid, 5=1-amino cyclopentanoic acid, *=$C_\alpha$-Me-L-Phenylalanine. The conserved motif=YXXXXL,Φ where Φ signifies any hydrophobic residue).

FIG. 2 shows the fluorescence-based thermal stability assay (FTS) results of the peptides and modified peptides described herein. Estimated $K_d$s extrapolated from the thermal shifts. * denotes experiments carried out with 200 µM of the relevant peptide.

FIG. 3A shows the determined $K_d$ values, binding enthalpy, and calculated entropy of eIF4G1 peptide, "eIF4G1" (SEQ ID NO: 8), modified eIF4G1 peptides "Tr2" (SEQ ID NO: 18), "Tr2_me5_1" (SEQ ID NO: 36) and "eIF4G1_me5" (SEQ ID NO: 39).

FIGS. 7B to 7E show the luciferase activity of the respective modified eIF4G1 peptides as described herein in MCF-7 5'UTR_MYC_Gaussia reporter cell line. FIG. 7B shows treatment of MCF-7 5'UTR_MYC_Gaussia reporter cell line with TAT_eIF4G1 (SEQ ID NO: 40) and equivalent control peptide TAT_eIF4G1_Cntrl (SEQ ID NO: 41); FIG. 7C shows treatment of MCF-7 5'UTR_MYC_Gaussia reporter cell line with TAT_eIF4G1_me5 (SEQ ID NO: 42) and equivalent control peptide TAT_eIF4G1_Cntrl (SEQ ID NO: 41); FIG. 7D shows treatment of MCF-7 5'UTR_MYC_Gaussia reporter cell line with water soluble GT_eIF4G1 modified peptide (SEQ ID NO: 44); FIG. 7E shows treatment of MCF-7 5'UTR_MYC_Gaussia reporter cell line with water soluble GT_eIF4G1_me5 modified peptide (SEQ ID NO: 46). Measurements were made in triplicate, and the p value of the statistical significance of differences in FIGS. 7B to 7E between the respective modified eIF4G1 peptides and control treatments at 30 µM stated. Experiments were carried out independently twice. Relative values were calculated using either the DMSO control or PBS mock treatment in the case of the TAT derivative peptides. The p value in FIG. 7D shows there is no significant difference between the unmodified GT_eIF4G1 peptide (SEQ ID NO: 44) and its control (SEQ ID NO: 45) in contrast to the other peptides.

FIG. 8A shows TAT_eIF4G1 (SEQ ID NO: 40) control peptide (SEQ ID NO: 41) and TAT peptide (SEQ ID NO: 7) treatment, FIG. 8B shows TAT_eIF4G1_me5 (SEQ ID NO: 42) treatment with respective control peptide (SEQ ID NO: 43) and TAT peptide (SEQ ID NO: 7), FIG. 8C shows GT_eIF4G1 (SEQ ID NO: 44) and equivalent control peptide (SEQ ID NO: 45) and FIG. 8D shows GT_eIF4G1_me5 peptide (SEQ ID NO: 46) and equivalent control peptide (SEQ ID NO: 47). The results shown in FIGS. 8A to 8D are of triplicate assays, and the p value of the statistical significance of differences stated between the respective modified eIF4G1 peptides and control treatments at 30 µM. Experiments were carried out independently twice. Relative values were calculated using either the DMSO control or PBS mock treatment in the case of the TAT derivative peptides. The p value in FIG. 8C is not significant for the GT_eIF4G1 peptide compared to its control peptide, whilst the p value in FIG. 8D for the modified GT_eIF4G1_me5 peptide is marginally significant compared to its control with a value of 0.0416.

FIG. 9 shows the FACS analysis of propidium iodide (PI)-stained MCF-7 reporter cells treated with non TAT fused peptides reporting sub-G1, G1, S and G2 cell populations. The p value of the statistical significance of differences is stated for the GT_eIF4G1_me5 peptide (SEQ ID NO: 46) against its control GT_eIF4G1_me4_Cntrl (SEQ ID NO: 47) and for the control peptide treatment against the DMSO control. Experiments were carried out in triplicate triplicate and independently once.

FIG. 10 shows the FACs analysis of propidium iodide stained MCF-7 reporter cells treated with TAT fused peptides reporting sub G1, G1, S and G2 cell populations. The p value of the statistical significance of differences is stated for the modified eIF4G peptides against their respective controls and for the TAT peptide only treatment against the PBS mock. Experiments were carried out in triplicate and independently once.

FIGS. 12A to 12F show the flow cytometric analysis of ANNEXIN-staining of MCF-7 cells 48 hours after peptide treatment (30 μM). Cells incubated for 48 hours in the presence of TAT (SEQ ID NO: 7) and a PBS mock treatment included as controls. Percentages (%) indicate amount of cells stained with ANNEXIN. Measurements were made in triplicate, and the p value stated of the statistical significance of differences between the respective modified eIF4G1 peptides mentioned in FIG. 11 and control treatments at 30 μM. Experiments were carried out independently once.

FIG. 13A shows the determined $K_d$ values, binding enthalpy, and calculated entropy for TAT_eIF4G1 (SEQ ID NO: 40) and TAT_eIF4G1_me5 (SEQ ID NO: 42). FIG. 13B shows Isotherms for the respective peptides of FIG. 13A. Isotherms were fitted to a one-to-one binding model.

FIGS. 15A to 15F show the results for the WST-1 assay and the cap-dependent translation assay when the MCF-7 5'UTR_MYC_Gaussia reporter cell line was treated with the peptide series shown in the alignment in FIG. 15G. Measurements were made in triplicate and repeated independently twice, and the p value of the statistical significance of differences in between the respective modified eIF4G1 peptides and control treatments at 30 μM stated. Experiments were carried out independently twice. Relative values were calculated using the 1% DMSO control treatment.

FIG. 15G shows the peptide sequences of the modified eIF4G1 peptides used for the WST-1 assay and the cap-dependent translation assay.

DETAILED DESCRIPTION OF THE INVENTION

Figure 1A:
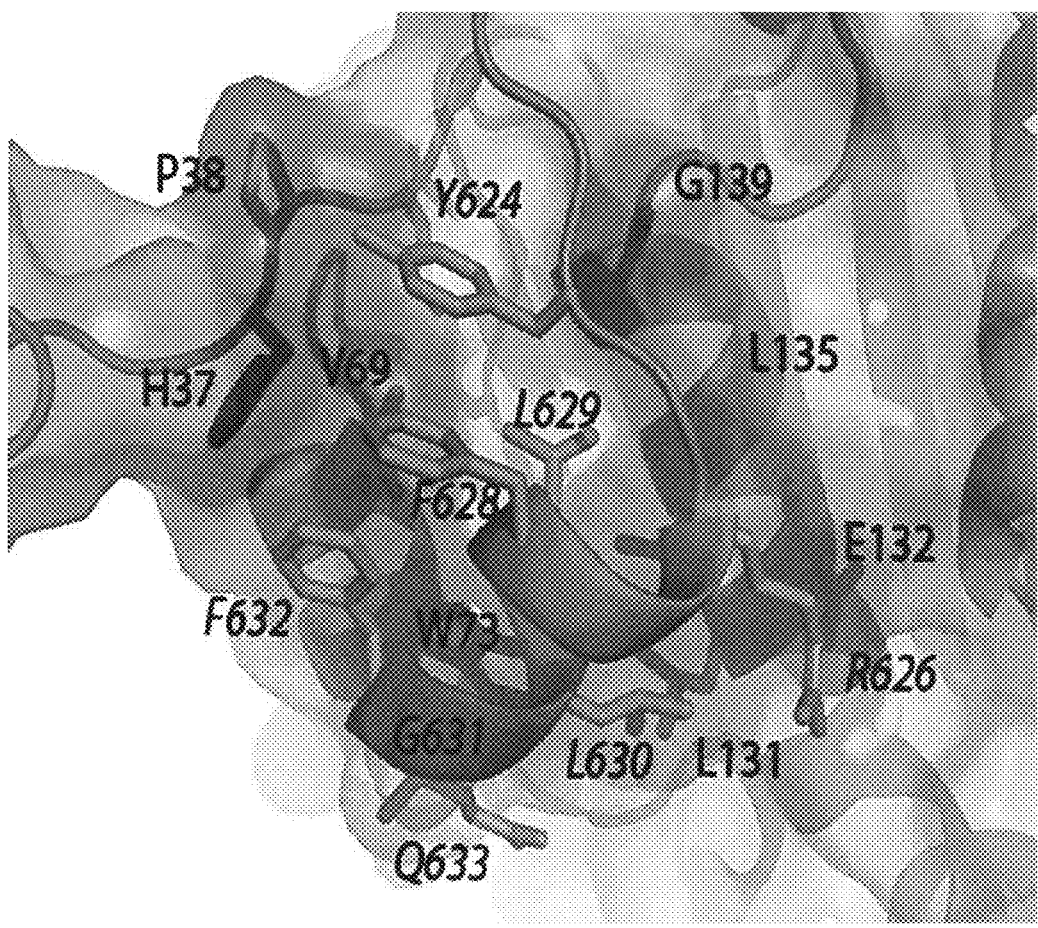
FIG. 1A shows the surface representation of eIF4E interacting with the eIF4GI peptide showing key eIF4E residues in blue and key peptide residues in purple. G631 is shown in red. eIF4E residues are labeled in italics.
Figure 3C:
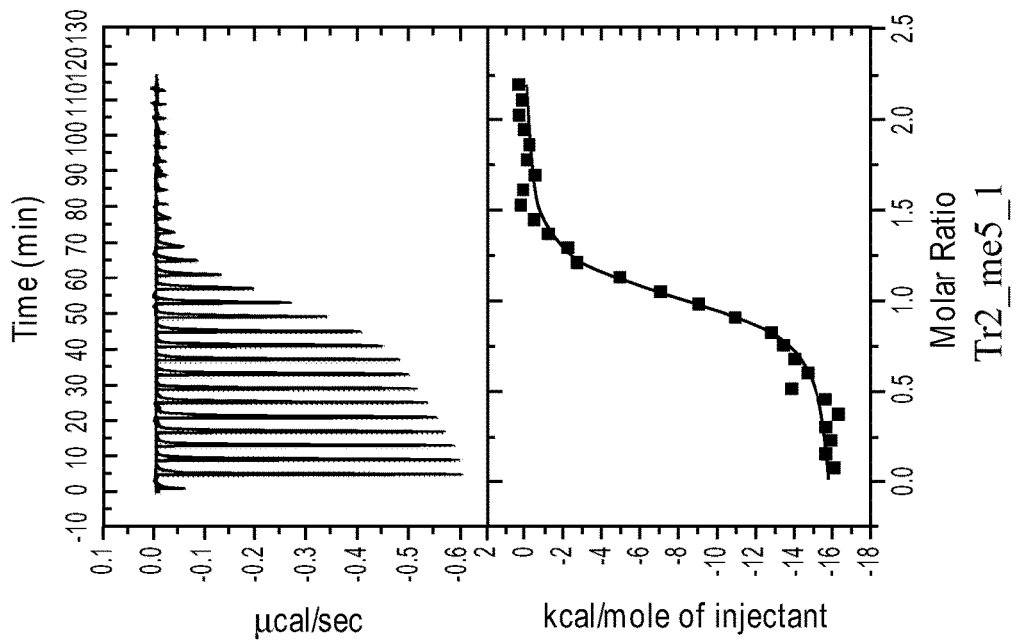
FIGS. 3B to 3E show the isotherms for the respective peptides described in FIG. 3A. Isotherms were fitted to a one-to-one binding model.
Figure 3B:
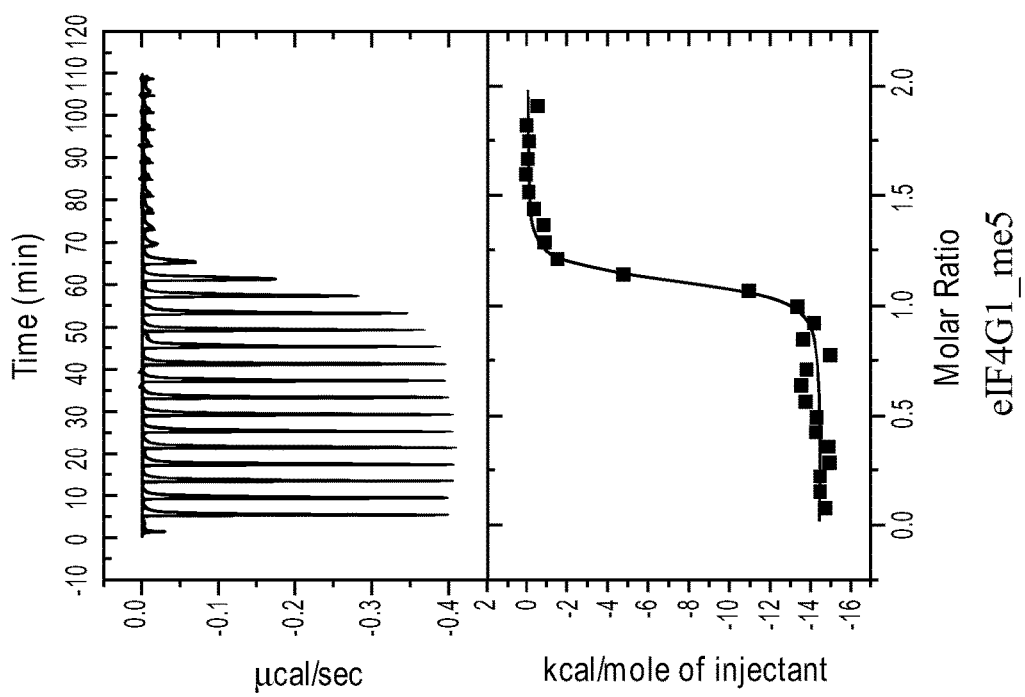
Figure 3E:
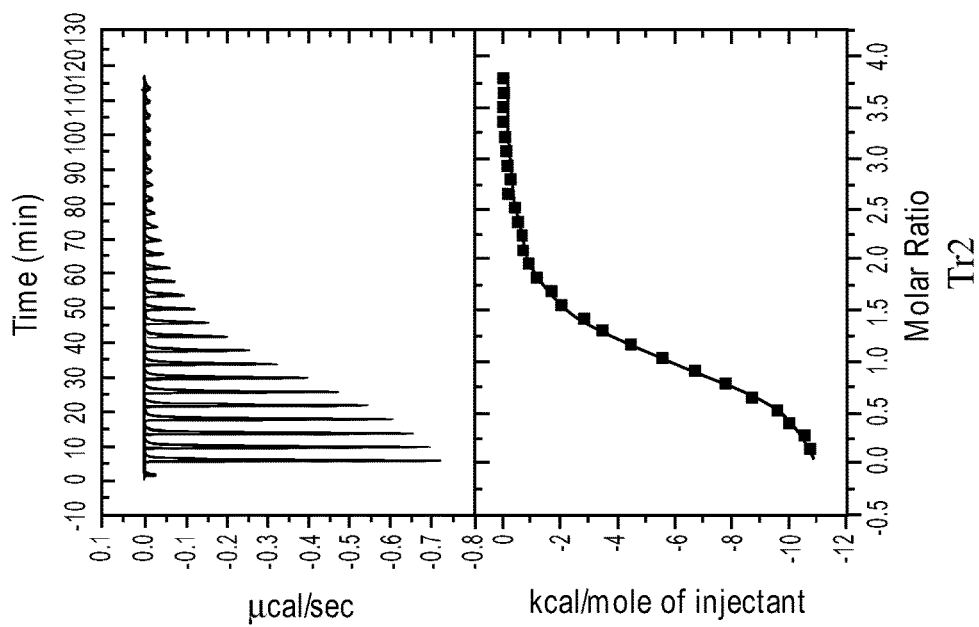
Figure 3D:
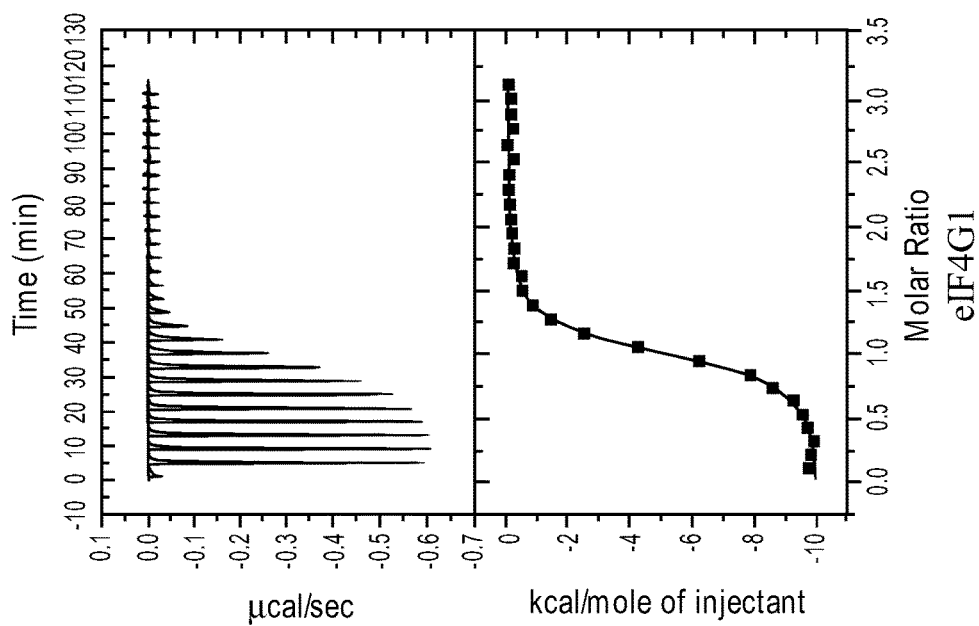

In the present invention, a modified eIF4G1 (eukaryotic translation initiation factor 4 gamma 1) peptide has been developed, with at least one α-helix inducing residue, where the helix observed upon binding eIF4E in the reported crystal structures is retained in solution, as shown by CD studies and inferred by molecular dynamic simulations. The inventors also found that the modified eIF4GI peptide binds with an apparent $K_d$ of 9.43±2.57 nM, which is ~15.7 fold more potent than the template peptide from which it is designed. In addition, the modified eIF4G1 peptide showed significant biological activity such as inhibition of cap-dependent translation in MCF-7 cells, which were stably transfected with a c-myc based reporter system, at a concentration of 300 μM and 400 μM. The wild-type peptide and the modified eIF4G1 peptide when fused to the cell penetrating TAT peptide showed inhibition of the cap-dependent translation in MCF-7 cells at much lower concentrations. In particular, the modified eIF4G1 peptide has been shown to inhibit cap dependent translation and cause cell death in MCF-7 cells at high micromolar concentration and the same peptide when fused to TAT has also been shown to be more potent than the eIF4G1 template peptide (wild type). Propidium Iodide staining revealed that the TAT fused modified eIF4G1 peptide caused more cell death than the TAT fused eIF4G1 template peptide with substantial decreases in the G1 and G2 cell populations. Also annexin staining experiments indicated that in the case of the TAT fused modified eIF4G1 peptides that cell death occurred through apoptosis. For example, the data in FIGS. 15A to 15G also links the affinity of the modified eIF4G1 peptides to its ability to achieve significant inhibitory effects in the cap dependent and WST-1 assays.

The results presented herein indicate that stabilization of the eIF4G helix is feasible and results in dramatically higher affinity of the peptide towards eIF4E, as well as imparting some biological activity even in the absence of a TAT tag. The inventors have thus found that the modified eIF4G peptide of the present invention is a potent binder of eIF4E compared to other inhibitors known in the literature, and with it possessing some biological activity indicating cell permeability, represents an excellent starting point for drug development. The observations made by the inventors and disclosed herein are useful in the design of new eIF4E inhibitors for therapeutic applications, for example, in the treatment of autism or cancer.

"eIF4E" or "eIF4E protein" are used interchangeably and refer to the human mature wild type eIF4E protein with the accession No. PO6730 (UNIPROT Number).

"Peptide" relates to a molecule consisting of at least two amino acids that are covalently bound to each other via a peptide bond. Peptides may be fragments of proteins and may, for example, comprise 2-200, 2-100, 2-50, or 2-20 amino acids In one aspect, the present invention relates to a modified eIF4G1 peptide, wherein the peptide has been modified to stabilize the α-helix.

In some embodiments, the modified eIF4G1 peptide of present invention can be derived from the mature wild type eIF4G1 sequence of a mammal or non-mammal species. It can, for example be of human, porcine, murine, bovine, or rat origin. In preferred embodiments, the modified eIF4G1 peptide is derived from the mature human wild-type eIF4G1 protein (Swiss Prot Accession No. Q04637) with the amino acid sequence KKRYDREFLLGFQF (SEQ ID NO: 8).

An "α-helix" used herein refers to a three dimensional structural conformation which is analogous to those found in proteins and polypeptides. The α-helix conformation found in naturally occurring proteins and polypeptides has its side chains extending to the outside of the structure, has a complete turn every 3.6 amino acids, is right-handed and typically has hydrogen bonding between the carbonyl groups of the amide bond and an amide N—H group 4 amino acids further on in the sequence. The cyclic peptides of the present invention have a helicity calculated from molar elipticities obtained from circular dichroism spectroscopy (CD spectroscopy) and are expressed as a percentage of the theoretical helicity obtainable for that peptide or a relative helicity compared to a reference standard or standard helix.

In an embodiment of the above aspect of the invention, the modified eIF4G1 peptide comprises at least one α-helix inducer. Any α-helix inducer known in the art can be used according to the methods of the invention as long as the α-helix of the modified eIF4G1 peptide can be stabilized. Exemplary α-helix inducers can include but are not limited to unnatural amino acids including 2-aminoisobutyric acid or α-aminoisobutyric acid (Aib), transition metals such as $Cu^{2+}$, $Zn^{2+}$, $Cd^{2+}$, $Ru^{3+}$, $Pd^{2+}$ capable of binding both acidic and basic residues to achieve helix stabilization, chelated divalent metal ions, disulfide bridges, lactam-type bridges, aliphatic linkers, to mention only a few.

The modified eIF4G1 peptide of the invention can be a fragment of any length as long as the α-helix of the modified eIF4G1 is stabilized and without disrupting the desired function of the modified eIF4G1 peptide. In some embodiments, the modified eIF4G1 peptide of the invention can for example, comprise 2 to 35 amino acids; 2 to 30 amino acids; 2 to 25 amino acids; 2 to 20 amino acids; 2 to 10 amino acids; 5 to 35 amino acids; 10 to 35 amino acids; 15 to 35 amino acids; 30 amino acids; 27 amino acids; 25 amino acids; 24 amino acids; 22 amino acids; 20 amino acids; 18 amino acids; 17 amino acids; 16 amino acids; 15 amino acids; 14 amino acids; 13 amino acids; 12 amino acids; 11 amino acids; 10 amino acids; 9 amino acids; 8 amino acids; or 7 amino acids. The amino acids incorporated into the amino acid sequences of the present invention may be L-α-amino acids, D-α-amino acids or mixtures thereof.

In one embodiment, the modified eIF4G1 peptide can comprise, consist essentially of or consist of the amino acid sequences set forth in SEQ ID NO: 1 (K**RE**FQF), or SEQ ID NO: 2 (KKRYDRE*LL*FQF), or SEQ ID NO: 3 (KKR*DRE**LG*QF), or SEQ ID NO: 4 (KKRYDRE*LLGFQF).

In one embodiment, the modified eIF4G1 peptide of the present invention can also comprise one or more peptides other than the eIF4G1 peptide. This peptide can for example be a cell penetrating (permeable) peptide, a protein tag, a linker, in which a fusion protein or peptide containing the modified eIF4G1 peptide is also part of the invention. The modified eIFG1 peptide of the present invention can also comprise any suitable fusion partner, for example, alkaline phosphatase or the green fluorescent protein (GFP) as long as the fusion partner does not interfere with the α-helix stabilizing properties of the peptide. A fusion partner appropriate for therapeutic purpose is a protein such as albumin which can enhance the in vivo (circulation) half-life of the modified eIF4G1 peptide of the invention. The fusion partner can be fused to the N-terminus of the modified eIF4G1 peptide. Likewise any peptide tag can be fused to the N-terminus of the modified eIF4G1 peptide as long as its α-helix stabilizing properties are maintained. Examples of suitable affinity tags are the Strep-Tag®, the Flag-tag or the myc-tag, all of which can be used for purification of the modified eIF4G1 peptide by affinity chromatography.

Any cell penetrating peptide known to persons skilled in the art can be used in the present invention as long as it is capable of translocating the modified eIF4G1 peptide across the cell membrane without disrupting the desired function of the peptide modified peptide. Cell-penetrating peptides are generally short polycationic polypeptides, and exemplary cell penetrating peptides can include but are not limited to Penetratin®, HIV-1 Tat protein, HIV-1 Rev protein, Arg9 (polyarginine), pIs1-1, a membrane-translocating sequence (MTS; see, Fawell S, et al., Proc. Natl. Acad. Sci. USA 91:664-668 (1994)), an integrin h-region, a multiple antigenic peptide (MAP; see, Tam J, Proc. Natl. Acad, Sci. USA, 85:5409-5413 (1988).), Herpes Simplex Virus VP22 protein, Influenza Virus HA-2 protein and Bac (1-15, 15-24), to mention only a few. A non-specific example of a TAT peptide used herein is YGRKKRRQRRR (SEQ ID NO: 42) or derivatives thereof known in the art.

The modified eIF4G1 peptide of the present invention can also be conjugated to a protein or different chemical (macromolecular) moiety via a suitable peptidic or non-peptidic linker that can be attached to any residue within the primary sequence of the modified eIF4G1 peptide. A protein can, for example, be conjugated with the modified eIF4G1 peptide using solvent exposed α-amino groups of lysine residues and glutaraldehyde as linker. Another suitable coupling chemistry is amine-amine crosslinking using bis(succinimidylesters) of 5'5'-dithiobis-(2-nitrobenzoic acid) (DNTB) known to persons skilled in the art.

In some embodiments, the modified eIF4G1 peptide can for example be conjugated to a poly(alkylene glycol), such as a PEG (polyethylene glycol) group, to make the compound more easily formulated and orally available. The amphiphilic nature of PEG helps protect the parent peptide from enzymatic breakdown and positions the drug for absorption across the gastrointestinal tract into the plasma. The poly(alkylene glycol), suitably an activated poly(alkylene glycol), can be reacted with a facilitator such as an amino acid, e.g. lysine, to form a covalent bond. Such a conjugation process is called "pegylation" and can be for example be carried out using poly(ethylene glycol) or derivatives thereof, such as methoxy poly(ethylene glycol), or any other useful poly(alkylene glycol), such as, for example poly(propylene glycol). The chemical moieties for derivitization may also be selected from water soluble polymers such as polyethylene glycol, ethylene glycol/propylene glycol copolymers, carboxymethylcellulose, dextran, polyvinyl alcohol and the like. The pentapeptide compounds may be modified at random positions within the molecule, or at predetermined positions within the molecule and may include one, two, three or more attached chemical moieties. In some embodiments, the modification occurs at a position outside of the cyclic pentapeptide moiety, for example at amino acids preceding the cyclic pentapeptide moiety or at the N-terminus.

The polymer may be of any molecular weight, and may be branched or unbranched. For polyethylene glycol, exemplary examples include micropegylated groups devised specifically to enhance oral delivery in peptides as described in WO2004047871. Methods for attaching Peg groups are well described in the patent literature (WO2004047871, U.S. Pat. No. 5,643,575; EP 0 401 384; WO03057235A2) For example, polyethylene glycol may be covalently bound through amino acid residues via a reactive group, such as, a free amino or carboxyl group. Reactive groups are those to which an activated polyethylene glycol molecule may be bound. One or more reaction chemistries may be employed to attach polyethylene glycol to specific amino acid residues (e.g., lysine, histidine, aspartic acid, glutamic acid, or cysteine) of the polypeptide or to more than one type of amino acid residue (e.g., lysine, histidine, aspartic acid, glutamic acid, cysteine and combinations thereof) of the protein or polypeptide. Polyethylene glycol may be attached to the protein or polypeptide either directly or by an intervening linker. Polyethylene glycol can also be attached to polypeptides using a number of different intervening linkers. For example, U.S. Pat. No. 5,612,460 discloses urethane linkers for connecting polyethylene glycol to proteins. Protein polyethylene glycol conjugates wherein the polyethylene glycol is attached to the protein or polypeptide by a linker can also be produced by reaction of proteins or polypeptides with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number of additional polyethylene glycol derivatives and reaction chemistries for attaching polyethylene glycol to proteins and polypeptides are described in WO 03/057235; PCT/GB03/00062; U.S. Pat. No. 5,428,128; U.S. Pat. No. 6,127,355; and U.S. Pat. No. 5,880,131.

A "linker" refers to a molecule or a group of molecules, for example a peptidic or non-peptidic linker which is capable of connecting two molecules (peptides). In some embodiments, the linker can refer to any kind of linker including a branched or unbranched peptide linker known in the art. Such a linker can for example comprise two, three, or four amino acid residues. The amino acid residues making up a peptide linker can be independently selected from the group of amino acids, preferably naturally occurring amino acids. The naturally occurring amino acids are alanine (Ala), arginine (Arg), asparagine (Asn), aspartic acid (Asp), cysteine (Cys), glutamic acid (Glu), glutamine (Gln), glycine (Gly), histidine (His), isoleucine (Ile), leucine (Leu), lysine (Lys) methionine (Met), ornithine (Orn), phenylalanine (Phe), proline (Pro), serine (Ser), threonine (Thr), tryptophan (Trp), tyrosine (Tyr), and valine (Val). Certain non-naturally occurring amino acids also can be part of the peptide linker. Such non-naturally occurring amino acids can include any of the non-naturally occurring acids described herein and are not limited to citrulline (Cit) and protected amino acids such as naturally occurring amino acids protected with groups such as acetyl, formyl, tosyl, nitro and the like. Exemplary peptide linkers that can be used include Phe-Lys, Val-Lys, Phe-Phe-Lys, Lys-Phe-Lys, Gly-Phe-Lys, Ala-Lys, Gly-Thr, to mention only a few. Any of the linker mentioned herein can for example be coupled to the N-terminus (amino group) or the C-terminus of an eIF4G1 peptide or a modified eIF4G1 peptide described herein. Linkage of the peptide sequence(s) described herein may be performed by any of several well known methods in the art.

In some embodiments, the modified eIF4G1 peptide can comprise, consist essentially of or consist of the following (amino acid) sequences:

```
                                        (SEQ ID NO: 2)
Linker-KKRYDRE*LL*FQF;

(SEQ ID NO: 5)
YDRE*LL5FQF;

(SEQ ID NO: 6)
KKRYDRE*LL5FQF;

(SEQ ID NO: 8)
YGRKKRRQRRR(SEQ ID NO: 7)-Linker-KKRYDREFLLGFQF; or (SEQ ID NO: 9).
YGRKKRRQRRR(SEQ ID NO: 7)-Linker-KKRYDRE*LL*FQF
```

In this context, "5" refers to 1-aminocyclopentanoic acid.

In other embodiments, the modified eIF4G1 peptide can comprise, consist essentially of or consist of the (amino acid) sequences:

```
Linker-KKRYDREFLL*FQF(SEQ ID NO: 10)-NH2,

TKKRYDREFLL*FQF(SEQ ID NO: 11)-NH2,

KKRYDREFLL*FQF(SEQ ID NO: 10)-NH2,

KRYDREFLL*FQF(SEQ ID NO: 12)-NH2,

RYDREFLL*FQF(SEQ ID NO: 13)-NH2,

YDREFLL*FQF(SEQ ID NO: 14)-NH2,
```

```
                                        (SEQ ID NO: 15)
KIIYDREFLLGFQF,
or (SEQ ID NO: 16)
KKRYTREFLLGFQG.
```

"*" or "Xaa" referred to in the peptides described herein can be used interchangeably and can be any kind of amino acid known in the art, for example naturally occurring and non-naturally occurring (synthetic) amino acids. Xaa can for example be a D- or L-alpha amino acid residue. The modified eIF4G1 peptide described herein can have at least one Xaa that is favorable to helix formation or is capable of stabilizing the α-helix of the peptide. In some embodiments, Xaa can be a cycloalkane derivative. A cycloalkane derivative can for example be 1-aminocyclopentanoic acid, 1-aminocyclohexanoic acid, β-cyclohexylalanine, an α-(1-carboxycyclopentyl)glycine, 1-aminocyclopropanoic acid, 1-amino cyclobutanoic acid, or aminomethylcyclohexanoic acid, to mention only a few.

Amino acids known in the art (both naturally occurring and synthetic) which can be used for the peptides and/or modified peptides referred to herein (e.g. also for "*" or "Xaa") can include, but are not limited to 2-aminoadipic acid (Aad), aminobutyric acid (Abu), aminobenzoic acid (Abz), aminocyclohexanoic acid (Ac6c), aminocyclopentanoic acid (Ac5c), aminocyclopropanoic acid (Ac3c), aminodecanoic acid (Adc), aminododecanoic acid (Ado), aminohexanoic acid (Ahx), aminoisobutyric acid (Aib), alanine (Ala), alloisoleucine (AIle), allothreonine (aThr), aminomethylbenzoic acid (Amb), aminomethylcyclohexanoic acid (Amc), 2-amino-2-thiazolidine-4-carboxylic acid, aminononanoic acid, aminooctanoic acid, aminopentanoic acid (Avl), arginine (Arg), asparagine (Asn), aspartic acid (Asp), aminoundecanoic acid, aminovaleric acid, biphenylalanine, benzoylphenylalanine, carnitine, 4-cyano-2-aminobutyric acid, 3-cyano-2-aminopropionic acid, cyclohexylalanine, cyclohexylglycine, citruline (Cit), cysteine (Cys), cystine, 2,4-diaminobutyric acid (A2bu), 2,3-diaminopropionic acid (A2pr), diethylglycine, dihydrotryptophan, diaminobenzoic acid, dipropylglycine, 2,3-diaminopropionic acid, 2,3-didehydroalanine (Dha), (Z)-2,3-didehydroaminobutyric acid (Dhb), erythro-3-hydroxyaspartic acid (HyAsp), 2-aminobutyric acid (Abu), dolaproine (Dap), dolaisoluine (Dil), dolaisovaline (Dov), Hiv, methyl valine (MeVal), 3-amino-6-octyneoic acid (Doy), dolaphenine (Doe), dolahexanoic acid (Dhex) 2-methyl-3-aminoisocaproic acid (Dml, dolamethylleuine), 2-amino-4-phenylisovaleric acid (Dpv, dolaphenvaline), diethylglycine, dihydrotryptophan, gamma-carboxyglutamic acid, glutamine (Gln), glutamic acid (Glu), glycine (Gly), histidine (His), homoarginine, homocysteine (Hcy), homophenylalanine, homoserine (Hse), homoserinelactone (Hsl), homotyrosine, hydroxylysine (Hyl), hydroxyproline (Hyp), 2-indolinecarboxylic acid, 2-indanylglycine, isoglutamine (iGln), isoleucine (Ile), indoleglycine, isonipecotic acid, isovaline (Iva), leucine (Leu), lysine (Lys), β-mercapto-β,β-cyclopentamethylenepropanoic acid, methionine (Met), methionine S-oxide (Met(O)), muramicacid (Mur), napthylalanine, neuraminicacid (Neu), norleucine (Nle), norvaline (Nva), octahydroindolecarboxylic acid, ornithine (Orn), pyridylalanine, penicillamine, pyroglutamic acid, phenylalanine (Phe), $C_\alpha$-Me-L-Phenylalanine, phenylglycine, phosphoserine (Ser (P)), pipecolic acid, 4-phosphomethylphenylalanine, propargylglycine, proline (Pro), putrescine, sarcosine (Sar), serine (Ser), statine (Sta), statine analogs, taurine (Tau), thiazolidinecarboxylic acid, tetrahydroisoquinoline-3-carboxylic acid, tert-leucine, threonine (Thr), thyroxine (Thx), tryptophan (Trp), tyrosine (Tyr), 3,5-diiodotyrosine (Tyr ($I_2$)), valine (Val) and AEEA. Abbreviations for amino acids, as used herein, are in accordance with the IUPAC guidelines on nomenclature (Nomenclature and Symbolism for Amino Acids and Peptides. *Eur. J. Biochem.* 138:9-37(1984)).

In some embodiments, the modified eIF4G1 peptide can comprise a protection group. It should be appreciated by those skilled in the art of peptide synthesis that any protection groups can be used. Examples of protection groups can include but are not limited to Fmoc (9-fluorenylmethoxycarbonyl) group, carbamate protecting groups such as Cbz (benzyloxycarbonyl), RCbz (benzyloxycarbonyl groups substituted on the aromatic ring), 9(2-sulfo)fluorenylmethylcarbamate, 9(2,7-dibromo)fluorenylmethylcarbamate, 2-chloro-3-indenylmethylcarbamate, Benz[f]inden-3-ylmethylcarbamate, Alloc (Allyloxycarbonyl), acyl, acetyl, benzoyl or benzyl.

In some embodiments, the modified eIF4G1 peptide can comprise at least one capping group at the N-terminus and/or the C-terminus. The capping group at the N-terminus of the modified eIF4G1 peptide usually has hydrogen atoms able to form hydrogen bonds or having a negative charge at the N-terminus to match with the helix dipole, a non-peptidic group or a mimic of an amino acid side chain. Suitable N-terminal capping groups include acyl such as acetyl, or N-succinate. The C-terminal capping group usually has hydrogen atoms able to form hydrogen bonds or having a positive charge at the C-terminus to match with the helix dipole. A suitable C-terminal capping group is an amide group or $NH_2$.

In some embodiments, the modified eIF4G1 peptide can comprise at least one non-natural amino acid including any of the non-natural amino acids described herein. Within the context of this embodiment, one or more phenylalanine residues (F) of the modified eIF4G1 peptide can be methylated at $C_\alpha$. In specific embodiments, one or more phenylalanine residues (F) in the peptide sequence KKRYDREFLLGFQF (SEQ ID NO: 8) is methylated at $C_\alpha$.

In some embodiments, one or more glycine residues (G) of the modified eIF4G1 peptide is replaced by a cycloalkane derivative. Examples of a cycloalkane derivative that can be used in the peptides described herein can include but are not limited to 1-aminocyclopentanoic acid, 1-aminocyclohexanoic acid, β-cyclohexylalanine, an α-(1-carboxycyclopentyl)glycine, 1-aminocyclopropanoic acid, and aminomethylcyclohexanoic acid.

In some embodiments, the modified eIF4G1 peptide of the invention can comprise a modified N-terminus. Methods for modification of the N-terminus of a peptide are within the knowledge of the person skilled in the art. Examples of modifying the N-terminus of the peptide can include acetylation, methylation, deamination, carboxylation, carbamoylation, glucuronylation, deamination of a side chain of a terminal amino acid, phosphorylation, deamination of the amino acid $C_\alpha$, glycosylation, formylation, myristoylation, peptide cyclization (e.g. using disulfide bridge) and palmitoylation, to mention only a few. The peptide backbone can be further modified by N-alkylation using groups such as methyl and ethyl.

In some embodiments, the modified eIF4G1 peptide of the invention can comprise a modified C-terminus, Methods for modification of the C-terminus of a peptide are within the knowledge of the person skilled in the art. Examples of modifying the C-terminus can include methylation, glycosylation, and prenylation, amidation, phosphorylation, peptide cyclization (e.g. using disulfide bridge), and addition of OEt, OBzl, OtBu, TBzl, or p-nitroaniline, to mention only a few.

In some embodiments, the modified eIF4G1 peptide can comprise one or more phenylalanine variants. Examples of a phenylalanine variant can include but is not limited to N-(α-fluoro-4-methylcinnamoyl)phenylalanine, p-fluorophenylalanine, m-fluoro-phenylalanine, and o-fluoro-phenylalanine.

In some embodiments, the modified eIF4G1 peptide can comprise any of the peptides selected from the group consisting of:

```
Tr2_AIB3_A5C:
                                               (SEQ ID NO: 28)
YDREFLL5FQF,

Tr2_me5_1:
                                               (SEQ ID NO: 36)
YDRE*LL5FQF, eIF4G1_me5:
                                               (SEQ ID NO: 39)
KKRYDRE*LL5FQF,

TAT_eIF4G1_me5:
                                               (SEQ ID NO: 42)
YGRKKRRQRRRGTKKRYDRE*LL5FQF,

GT_eIF4G1_me5:
                                               (SEQ ID NO: 46)
GTKKRYDRE*LL5FQF,

Ac 16 (Ac-G-T-K-K-R-Y-D-R-E-*-L-L-5-F-Q-F(SEQ ID NO: 46)-NH2),

Ac15 (Ac-T-K-K-R-Y-D-R-E-*-L-L-5-F-Q-F(SEQ ID NO: 48)-NH2), and

Ac14 (Ac-K-K-R-Y-D-R-E-*-L-L-5-F-Q-F(SEQ ID NO: 39)-NH2).
```

The present invention also provides a method of inhibiting eIF4E. The method includes administering of a pharmaceutically effective amount of a modified eIF4G1 peptide, wherein the peptide has been modified to stabilize the α-helix. In some embodiments, the modified eIF4G1 peptide can comprises at least one α-helix inducer. The method of the invention can in some embodiments include administering the pharmaceutically effective amount of the modified eIF4G1 peptide in a cell. Any cell may be used in the present method of the invention. In some embodiments, the cell is obtained or derived from a host organism, which may be any organism. The cell may be directly taken, e.g. isolated, from a respective host organism in form of a sample such as e.g. a biopsy or a blood sample. It may also have been obtained, e.g. isolated, from a host organism and subsequently been cultured, grown, transformed or exposed to a selected treatment. It may also for instance be present in the blood or in tissue, including in an organ, of the host organism. The host organism from which the cell is derived or obtained, including isolated, purified or enriched, or in which it is included, may be any organism such as a microorganism, an animal, such as a fish, an amphibian, a reptile, a bird, a mammal, including a rodent species, an invertebrate species, e.g. of the subclass Lissamphibia that includes e.g. frogs, toads, salamanders or newts, or a plant. Examples of mammals include, but are not limited to, a rat, a mouse, a rabbit, a squirrel, a vole, a platypus, a chicken, a cow, a goat, a sheep, a pig, a dog, a mouflon, a guinea pig, a hamster, a chimpanzee, a rhesus monkey a macque or a human.

In some embodiments, the cell used in the invention may be a tumor cell. In other embodiments, the tumor may derive from a cancer. Any forms of tumor or cancer may be used in the invention including for example, a benign tumor and a metastatic malignant tumor. Examples of tumors include, but are not limited to, haematological malignancies and solid tumours. Solid tumours include for instance a sarcoma, arising from connective or supporting tissues, a carcinoma, arising from the body's glandular cells and epithelial cells or a lymphoma, a cancer of lymphatic tissue, such as the lymph nodes, spleen, and thymus. Examples of a solid tumour include, but are not limited to, breast cancer, cervix cancer, lung cancer, a brain tumour, a neuroblastoma, colon cancer, rectal cancer, bladder cancer, a liver tumour, a pancreatic tumour, ovarian cancer, prostate cancer, esophagus cancer, melanoma, cancer of the head or neck and leukaemia.

The present invention also provides a method for the treatment or prevention of autism and cancer, comprising administering a pharmaceutically effective amount of a modified eIF4G1 peptide of the present invention or a pharmaceutical composition comprising a modified eIF4G1 peptide of the present invention. The present invention also provides a pharmaceutical composition or a medicament for use in the treatment or prevention of autism or cancer in a patient. The term "treat" or "treating" as used herein is intended to refer to providing an pharmaceutically effective amount of a modified eIF4G1 peptide of the present invention or a respective pharmaceutical composition or medicament thereof, sufficient to act prophylactically to prevent the development of a weakened and/or unhealthy state; and/or providing a subject with a sufficient amount of the complex or pharmaceutical composition or medicament thereof so as to alleviate or eliminate a disease state and/or the symptoms of a disease state, and a weakened and/or unhealthy state.

In some embodiments, the cancer to be treated can include but is not limited to breast cancer, lung cancer, head and neck cancer, esophagus cancer, skin cancer, bladder cancer, colon cancer, cervix cancer and prostate cancer.

The term "pharmaceutically effective amount" as used herein means that amount of a modified eIF4G1 peptide as described above or a pharmaceutical composition or medicament comprising the modified eIF4G1 peptide which is effective for producing some desired therapeutic effect in at least a sub-population of cells in the patient at a reasonable benefit/risk ratio applicable to any medical treatment.

The modified eIF4G1 peptide of the present invention can be formulated into compositions, for example pharmaceutical compositions, suitable for administration. Where applicable, a modified eIF4G1 peptide of the present invention may be administered with a pharmaceutically acceptable carrier. A "carrier" can include any pharmaceutically acceptable carrier as long as the carrier can is compatible with other ingredients of the formulation and not injurious to the patient. Accordingly, pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

Therefore, the present invention also provides a pharmaceutical composition comprising a one or more modified eIF4G1 peptide of the present invention.

A modified eIF4G1 peptide as described above or pharmaceutical composition or medicament thereof can be administered in a number of ways depending upon whether local or systemic administration is desired and upon the area to be treated. In some embodiments, the modified eIF4G1 peptide or the respective pharmaceutical composition thereof can be administered to the patient orally, or rectally, or transmucosally, or intestinally, or intramuscularly, or subcutaneously, or intramedullary, or intrathecally, or direct intraventricularly, or intravenously, or intravitreally, or intraperitoneally, or intranasally, or intraocularly.

The modified eIF4G1 peptides themselves may be present in the compositions in any of a wide variety of forms. For example, two or more peptides may be merely mixed together or may be more closely associated through complexation, crystallization, or ionic or covalent bonding. The modified eIF4G1 peptides of the invention can also encompass any pharmaceutically acceptable salts, esters, or salts of such esters, or any other compound, which, upon administration to an animal, including a human, is capable of providing the biologically active metabolite or residue thereof. Accordingly, also described herein is drawn to prodrugs and pharmaceutically acceptable salts of such pro-drugs, and other bioequivalents. The term "pharmaceutically acceptable salt" refers to physiologically and pharmaceutically acceptable salt(s) of the modified eIF4G1 peptides as described above; i.e. salts that retain the desired biological activity of the peptide and do not impart undesired toxicological effects thereto. Examples of such pharmaceutically acceptable salts include but are not limited to (a) salts formed with cations such as sodium, potassium, ammonium, magnesium, calcium, polyamines such as spermine and spermidine, etc; (b) acid addition salts formed with inorganic acids, for example hydrochloric acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chorine, bromine, and iodine.

In addition, the present invention also provides a nucleic acid molecule encoding for a modified eIF4G1 peptide of the present invention. In some embodiment, the nucleic acid molecule comprises a nucleotide sequence encoding a modified eIF4G1 peptide of the invention. Since the degeneracy of the genetic code permits substitutions of certain codons by other codons which specify the same amino acid and hence give rise to the same protein, the invention is not limited to a specific nucleic acid molecule but includes all nucleic acid molecules comprising a nucleotide sequence coding for the modified eIF4G1 peptides of the present invention.

The nucleic acid molecule disclosed herein may comprise a nucleotide sequence encoding the modified eIF4G1 peptide of the invention which can be operably linked to a regulatory sequence to allow expression of the nucleic acid molecule. A nucleic acid molecule such as DNA is regarded to be 'capable of expressing a nucleic acid molecule or a coding nucleotide sequence' or capable 'to allow expression of a nucleotide sequence' if it contains regulatory nucleotide sequences which contain transcriptional and translational information and such sequences are "operably linked" to nucleotide sequences which encode the polypeptide. An operable linkage is a linkage in which the regulatory DNA sequences and the DNA sequences sought to be expressed are connected in such a way as to permit gene sequence expression. The precise nature of the regulatory regions needed for gene sequence expression may vary from organism to organism, but shall, in general include a promoter region which, in prokaryotes, contains only the promoter or both the promoter which directs the initiation of RNA transcription as well as the DNA sequences which, when transcribed into RNA will signal the initiation of synthesis. Such regions will normally include non-coding regions which are located 5' and 3' to the nucleotide sequence to be expressed and which are involved with initiation of transcription and translation such as the TATA box, capping sequence and CAAT sequences. These regions can for example, also contain enhancer sequences or translated signal and leader sequences for targeting the produced polypeptide to a specific compartment of a host cell, which is used for producing a modified eIF4G1 peptide of the present invention.

The nucleic acid molecule comprising the nucleotide sequence encoding the modified eIF4G1 peptide of the invention can be comprised in a vector, for example an expression vector. Such a vector can comprise, besides the above-mentioned regulatory sequences and a nucleic acid sequence which codes for a modified eIF4G1 peptide of the invention, a sequence coding for restriction cleavage site which adjoins the nucleic acid sequence coding for the peptide in 5' and/or 3' direction. This vector can also allow the introduction of another nucleic acid sequence coding for a protein to be expressed or a protein part. The expression vector preferably also contains replication sites and control sequences derived from a species compatible with the host that is used for expression. The expression vector can be based on plasmids well known to person skilled in the art such as pBR322, puC16, pBluescript and the like.

The vector containing the nucleic acid molecule can be transformed into host cells capable of expressing the genes. The transformation can be carried out in accordance with standard techniques. Thus, the invention is also directed to a (recombinant) host cell containing a nucleic acid molecule as defined above. In this context, the transformed host cells can be cultured under conditions suitable for expression of the nucleotide sequence encoding the modified eIF4G1 peptide of the invention. Host cells can be established, adapted and completely cultivated under serum free conditions, and optionally in media which are free of any protein/peptide of animal origin. Commercially available media such as RPMI-1640 (Sigma), Dulbecco's Modified Eagle's Medium (DMEM; Sigma), Minimal Essential Medium (MEM; Sigma), CHO—S-SFMII (Invitrogen), serum free-CHO Medium (Sigma), and protein-free CHO Medium (Sigma) are exemplary appropriate nutrient solutions. Any of the media may be supplemented as necessary with a variety of compounds, examples of which are hormones and/or other growth factors (such as insulin, transferrin, epidermal growth factor, insulin like growth factor), salts (such as sodium chloride, calcium, magnesium, phosphate), buffers (such as HEPES), nucleosides (such as adenosine, thymidine), glutamine, glucose or other equivalent energy sources, antibiotics, trace elements. Any other necessary supplements may also be included at appropriate concentrations that are known to those skilled in the art.

As used herein, "nucleic acid" refers to any acid in any possible configuration, such as linearized single stranded, double stranded or a combination thereof. Nucleic acids may include, but are not limited to DNA molecules (e.g., cDNA or genomic DNA), RNA molecules (e.g., mRNA), analogues of the DNA or RNA generated using nucleotide analogues or using nucleic acid chemistry, cDNA synthetic DNA, a copolymer of DNA and RNA, oligonucleotides, and PNA (protein nucleic acids). DNA or RNA may be of genomic or synthetic origin and may be single or double stranded. A respective nucleic acid may furthermore contain non-natural nucleotide analogues and/or be linked to an affinity tag or a label. As used herein, nucleotides include nucleoside mono-, di-, and triphosphates. Nucleotides also include modified-nucleotides, such as, but not limited to, phophorothioate nucleotides and deazapurine nucleotides and other nucleotide analogs.

SPECIFIC ILLUSTRATIVE EMBODIMENTS

Identification of a Minimal Interaction Motif

Initial studies were carried out using the 14mer eIF4G1 sequence KKRYDREFLLGFQF (SEQ ID NO: 8). To identify the minimal motif required for a measurable response on the fluorescence-based thermal stability assay (FTS) several N-terminal and C-terminal truncated peptides were designed (Tr1 to Tr3 peptides, SEQ ID NOs 17 to 19, see FIG. 1B). Peptide Tr2 (SEQ ID NO: 18) was chosen as this peptide retained the sequence corresponding to the α-helix observed in the eIF4E-peptide complex crystal structures (residues 625-35, eIF4G2 numbering used) (Marcotrigiano, J., et al, (1999) Cap-dependent translation initiation in eukaryotes is regulated by a molecular mimic of eIF4G. *Mol Cell* 3, 707-16; Brown, C. J., et al (2009) Crystallization of eIF4E complexed with eIF4GI peptide and glycerol reveals distinct structural differences around the cap-binding site. *Cell Cycle* 8, 1905-11). This allowed helix-inducing strategies to be pursued in the design of more potent peptides. The systematic study of the influence of the flanking regions upon the eIF4G1 peptide affinity also revealed that the C-terminal region (GFQF) contributed more to binding than the N-terminal (KKR) when fused to the conserved eIF4E motif (see FIG. 2, peptides Tr1 to 3, SEQ ID NOs: 17 to 19). The conserved eIF4E motif region either by itself or with a single additional residue from either the N or C-terminal regions showed no observable binding on the FTS assay. Also if the conserved tyrosine is mutated to an alanine in the 11mer (control) peptide (SEQ ID NO: 20) all eIF4E binding is lost.

Identification of Sites for Helix Stabilization

Residues D625, E627, G631 and Q633 in the Tr2 peptide (SEQ ID NO: 18) were replaced sequentially with aminoisobutyric acid (Aib) a known α-helix inducer (see FIG. 2, peptides Tr2_AIB1 to 4; SEQ ID NOs: 21 to 24). Residues D625 (Tr2_AIB peptide, SEQ ID NO: 21), E627 (Tr2_AIB2 peptide, SEQ ID NO: 22) and G631 (Tr2_AIB3 peptide, SEQ ID NO: 23) were chosen for replacement as their side chains projected into the solvent and formed no critical interactions to eIF4E (see FIGS. 1A and 1B). AIB substitution of G631 (Tr2_AIB3 peptide, SEQ ID NO: 23) increased the $T_m$ (melting temperature) of eIF4E upon peptide binding, whilst replacement of E627 (Tr2_AIB2 peptide, SEQ ID NO: 22) abolished measurable peptide binding. Inclusion of AIB, instead of D625 (Tr2_AIB1 peptide, SEQ ID NO: 21) and Q633 (Tr2_AIB4 peptide, SEQ ID NO: 24), at these positions severely attenuated peptide binding. Upon identification of G631 as a site for helix stabilization a series of α-aminocycloalkane derivates were inserted at this position including alanine (see FIG. 2, peptides Tr2_AIB3_ALA to Tr2_AIB3_A5C; SEQ ID NOs: 25 to 28) again using the Tr2 peptide as a template. The affinity of the peptide interaction with eIF4E significantly increased with the use of the unnatural amino acid: 1-aminocyclopentanecarboxylic acid (A5C) at position 631 (SEQ ID NO: 28) when compared to smaller ring derivatives (see FIG. 2). Without wishing to be bound by theory, by increasing the ring size of the aminocycloalkanes, the phi and psi angles either side of the α-carbon were restricted further, forcing the peptide in a conformation more like that observed in the peptide-protein complex, and thus reducing the entropic cost of binding.

To examine the truncated eIF4G1 peptide now containing an aminocyclopentanoic acid at position 631 (Tr2_AIB3_A5C peptide, SEQ ID NO: 28) for further potential sites of modification an alanine scan was performed. No changes to the eIF4E recognition motif or the A5C modification were carried out in the scan (see FIG. 2, Tr2_ALA_A5C1 to 7, SEQ ID NOs: 29 to 35). Amino acid positions 625 (SEQ ID NO: 29), 627 (SEQ ID NO: 31) and 633 (SEQ ID NO: 34) were amenable to alanine substitution producing no significant increase or decrease in potency. Replacing the positively charged R626 with alanine (SEQ ID NO: 30) ($K_d$~14900 nM) results in a much less potent peptide in comparison to the parent peptide (SEQ ID NO: 28) ($K_d$~1450 nM). Substitution of all three phenylalanine residues (F628, F632 and F634) reduced the affinity of the peptide towards eIF4E with F634 exhibiting the least effect. The three dimensional structure of the peptide in the eIF4E complex structure was then further examined and several sites were identified where α-carbon methylation of the peptide backbone could be utilized to rigidify the peptide further. These sites corresponded to F628, F632 and F634. To ensure that the naturally occurring side chains of the phenylalanine residues were retained they were replaced with the α-carbon methylated amino acid $C_\alpha$-methyl-L-phenylalanine (Tr2_me5_1 to 3 peptides, SEQ ID NOs: 36 to 38). The inclusion of a $C_\alpha$methyl group at position F628 (SEQ ID NO: 36) drastically improved the affinity of the peptide to such an extent that it elicited a $T_m$ shift in eIF4E with a magnitude similar to the wild-type eIF4G1 peptide (see FIG. 2). In order to generate a high affinity eIF4E peptide the A5C substitution of position 631 and the $C_\alpha$-Me-L-Phenylalanine modification at position F628 were made in the original 14-mer eIF4G1 peptide, which was termed eIF4G1_me5 (SEQ ID NO: 39). These changes resulted in a peptide that induced a thermal shift in the magnitude of ~14° C. in the melting temperature of eIF4E, a 1.7-fold increase over the original 14-mer eIF4G1 peptide.

The Increase in Potency of the Tr2_Me5_1 (SEQ ID NO: 36) and eIF4G1_Me5 Peptides (SEQ ID NO: 39) Over their Respective Unmodified Template Peptides, Tr2 and eIF4G1, is Caused by Stabilization of the α-Helix.

ITC titrations revealed (see FIG. 3A) that the peptides eIF4G1 (SEQ ID NO: 8), the truncated Tr2 (SEQ ID NO: 18), the truncated modified Tr2_me5_1 peptide (SEQ ID NO: 36) and the modified 14mer eIF4G1_me5 peptide (SEQ ID NO: 39) bound eIF4E with $K_d$ values of 147.93±22.81 nM, 1041.20±65.83 nM, 145.99±22.81 nM, and 9.43±2.57 nM respectively (FIG. 3). Both the two modified eIF4G1 peptides compared to their template peptides have a ΔΔG of ~2.5 kcal $mol^{-1}$ and 1.6 kcal $mol^{-1}$ respectively. Without wishing to be bound by theory, this difference in the ΔΔGs suggests that the modifications are affecting the two peptides to differing extents in probably a length dependent manner. The far UV CD spectra of these respective peptides eIF4GI (14mer), Tr2, Tr2_me5_1 and eIF4G1_me5 were measured (see FIGS. 3B to 3E) to investigate whether prior helix formation before binding to eIF4E is responsible for the lower $K_d$s measured for the modified peptides. The spectra for the 14-mer eIF4G1 (SEQ ID NO: 8) and Tr2 peptides (SEQ ID NO: 18) revealed no significant helical structure in solution and produced no measurable CD signal. In contrast the plateaus at 220 nm and the shift in the minima of the spectra to 205 nm in the CD spectra of the modified eIF4G1 peptides, Tr2 me5_1 (SEQ ID NO: 36) and eIF4G1_me5 (SEQ ID NO: 39), indicate helical formation in solution. Without wishing to be bound by theory, these spectra show that the inclusion of A5C at position 631 and the $C_\alpha$-Me-L-Phenylalanine substitution at position 628 do indeed induce the formation of the eIF4G1 helix and presumably reduce the entropic cost of binding to eIF4E.

Molecular dynamic simulations were carried out to study the folding behavior of the modified and non modified eIF4G1 peptides described herein. The sequences of the eIF4G1 (SEQ ID NO: 8), Tr2 (SEQ ID NO: 18), Tr2_me5_1 (SEQ ID NO: 36) and eIF4G1_me5 (SEQ ID NO: 39) peptides were modeled initially in extended conformations and then peptide folding was simulated using the implicit solvent method. The simulations (200 ns on each peptide) showed that the eIF4G1_me5 (SEQ ID NO: 39) was predominately helical and that Tr2_me5_1 (SEQ ID NO: 36) was also significantly helical (see FIGS. 5 and 6A to 6D). The eIF4G1 (SEQ ID NO: 8) on the other hand exhibited relatively short stretches of helicity during the simulation, whilst the Tr2 peptide (SEQ ID NO: 18) displayed a short region of helical structure at the start of the simulation that was not maintained during the later stages of the trajectory. These simulations support the conclusion made from the circular dichroism experiments that the modified peptides are more helical in character.

If the enthalpies and entropies derived from the ITC experiments are examined it is noticeable that the helically stabilized peptides Tr2_me5_1 (SEQ ID NO: 36) and eIF4G1_me5 (SEQ ID NO: 39) have much more favorable enthalpies of −16.07-0.2 kcal $mol^{-1}$ and −14.45±10.11 kcal $mol^{-1}$ respectively than the unmodified peptides, eIF4G1 (SEQ ID NO: 8) and Tr2 (SEQ ID NO: 18), with −9.7±0.05 kcal $mol^{-1}$ and −10.95±0.13 kcal $mol^{-1}$ respectively. Without wishing to be bound by theory, the increase in favorable enthalpy can be explained by the less mobile structure of the peptide (it 'breathes' less when bound to the protein surface) allowing it to form more optimal interactions e.g. h-bonds, electrostatic, Van der Waals with the protein surface by acting as a distance restraint. The helically stabilized peptides also have much more unfavorable entropies in comparison to the unmodified peptides (see FIGS. 3A to 3D). At first these results would seem to run counter to the mechanism of entropic reduction for increasing the observed affinities of the modified peptides for eIF4E. However if the more mobile state of the unstabilized peptide is considered then it is reasonable to assume that it will expel more water molecules from the surface of eIF4E when binding compared to the preformed more compact helically stabilized peptides.

Figure 4A:
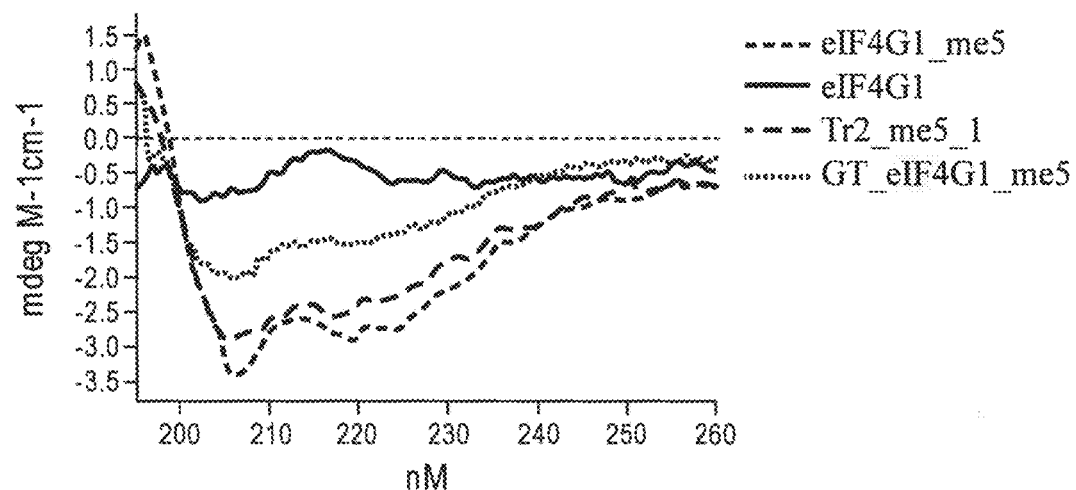
FIG. 4A shows a far-UV CD spectra of eIF4G1 peptide "eIF4G1" (SEQ ID NO: 8), modified eIF4G1 peptides "eIF4G1_me5" (SEQ ID NO: 39), "GT_eIF4G1_me5" (SEQ ID NO: 46) and "Tr2_me5_1" (SEQ ID NO: 36). Peptides "eIF4G1_me5" (SEQ ID NO: 39), "GT_eIF4G1_me5" (SEQ ID NO: 46) and "Tr2_me5_1" (SEQ ID NO: 36) show significant α-helical content compared to eIF4G1 with a pronounced minima at 205 nm and the development of a shoulder region at 220 nm.
Figure 4B:
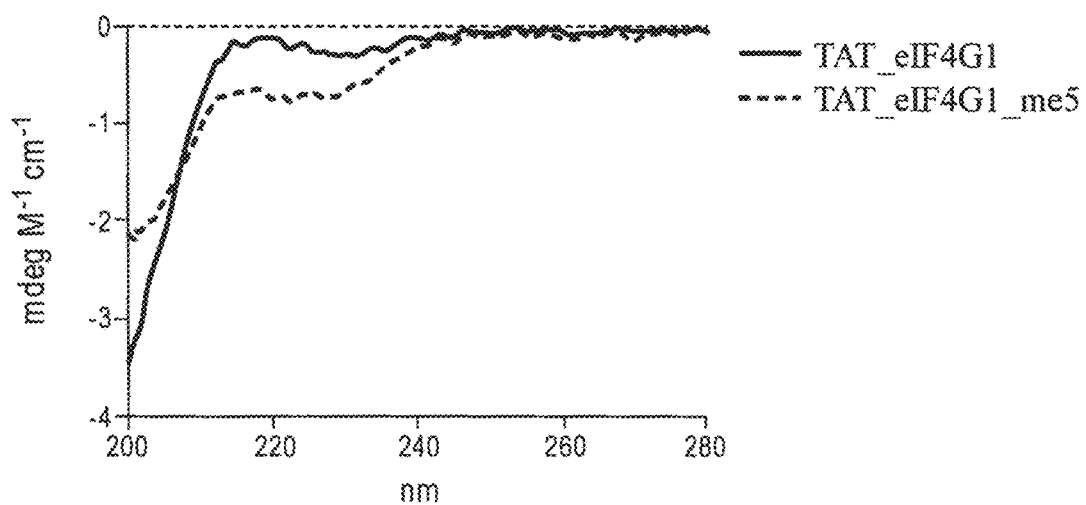
FIG. 4B shows a far-UV CD spectra for the eIF4G1 derivative peptides TAT-eIF4G1_me5 (SEQ ID NO: 42) and TAT_eIF4G1 (SEQ ID NO: 40). TAT_eIF4G1 shows a spectrum typical of random coil secondary structure whilst TAT_EIF4G1_me5 shows the development of a shoulder at 220 nm indicating partial helical character.
Figure 5:
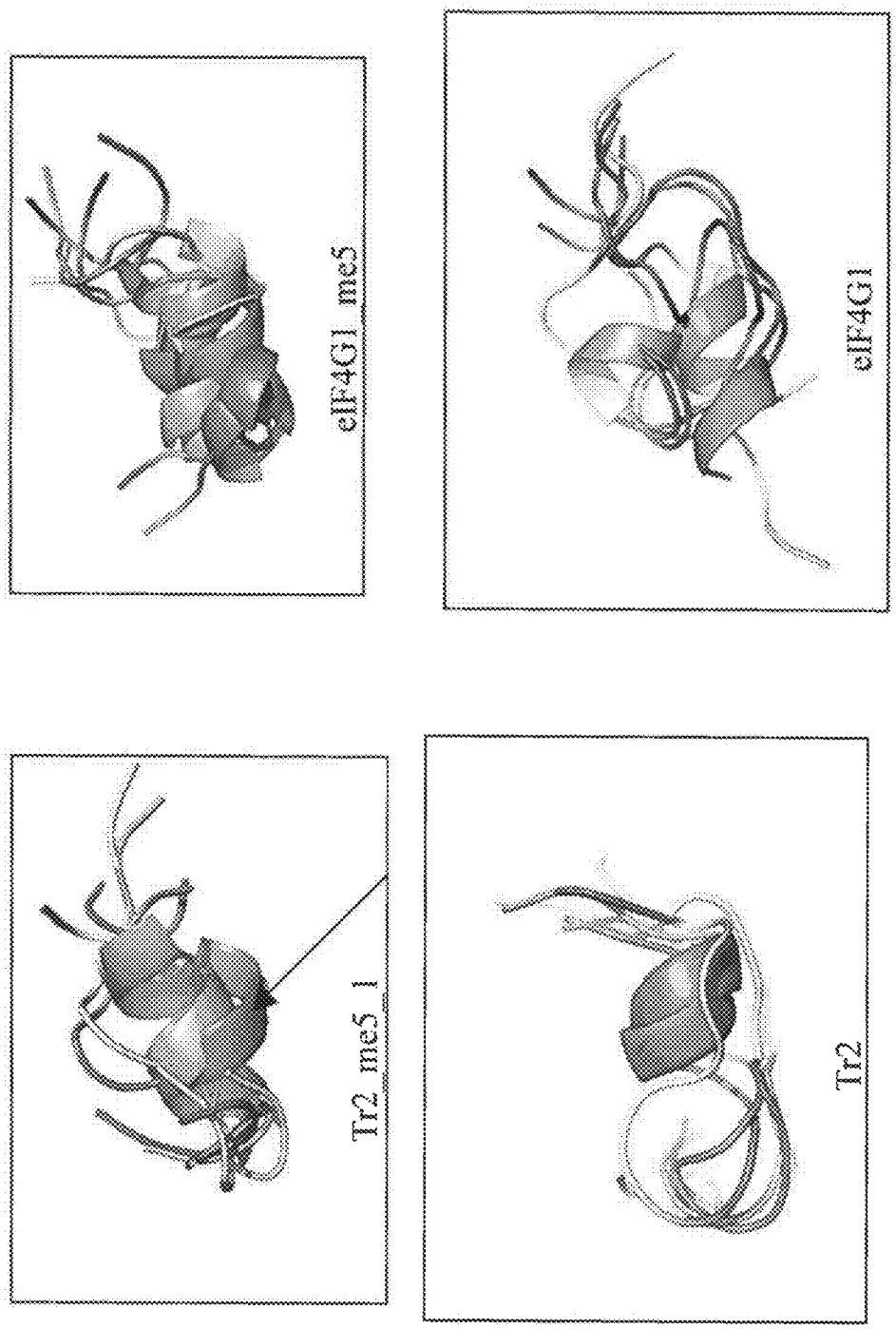
FIG. 5 shows MD simulations of "Tr2_me5_1" (SEQ ID NO: 36), "eIF4G1_me5" (SEQ ID NO: 39), "Tr2" (SEQ ID NO: 18) and "eIF4G1" (SEQ ID NO: 8) to examine the conformational space of the respective peptide. The arrow indicates the helix in α-helical conformation.
Figure 6A:
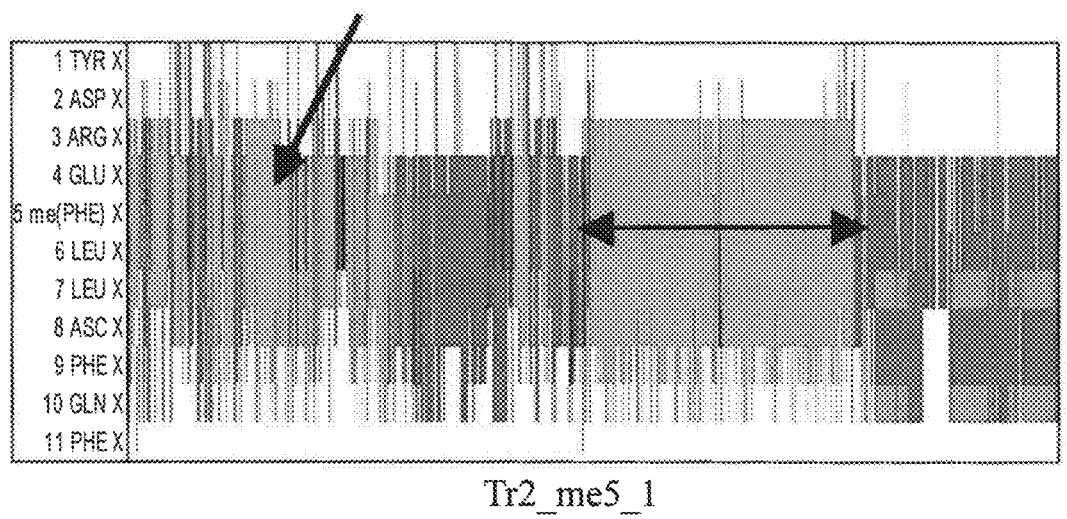
FIGS. 6A to 6D show the selected structures for peptide folding simulations. Colour code denotes position of structure in time in the computer simulation as depicted in the legend. The arrows indicate the helix in α-helical conformation.
Figure 6B:
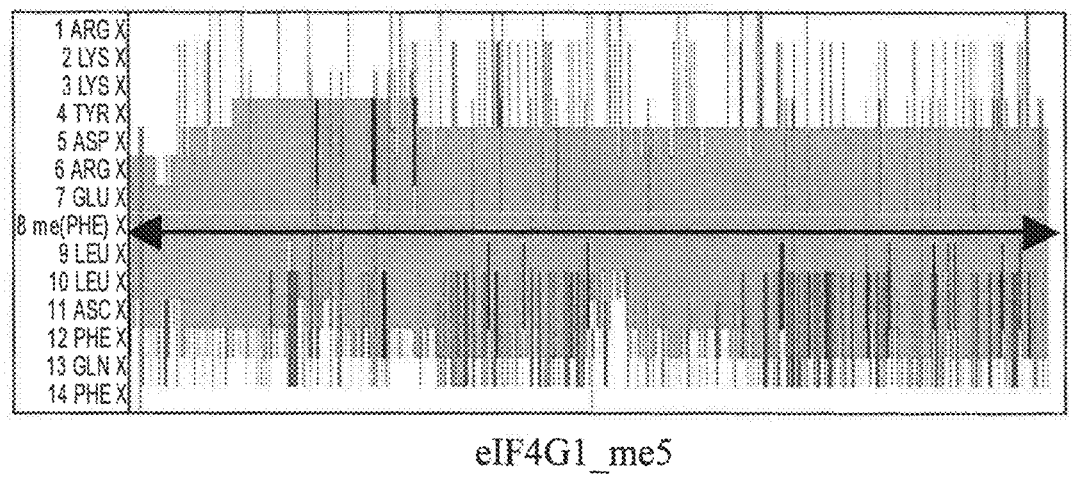
Figure 6C:
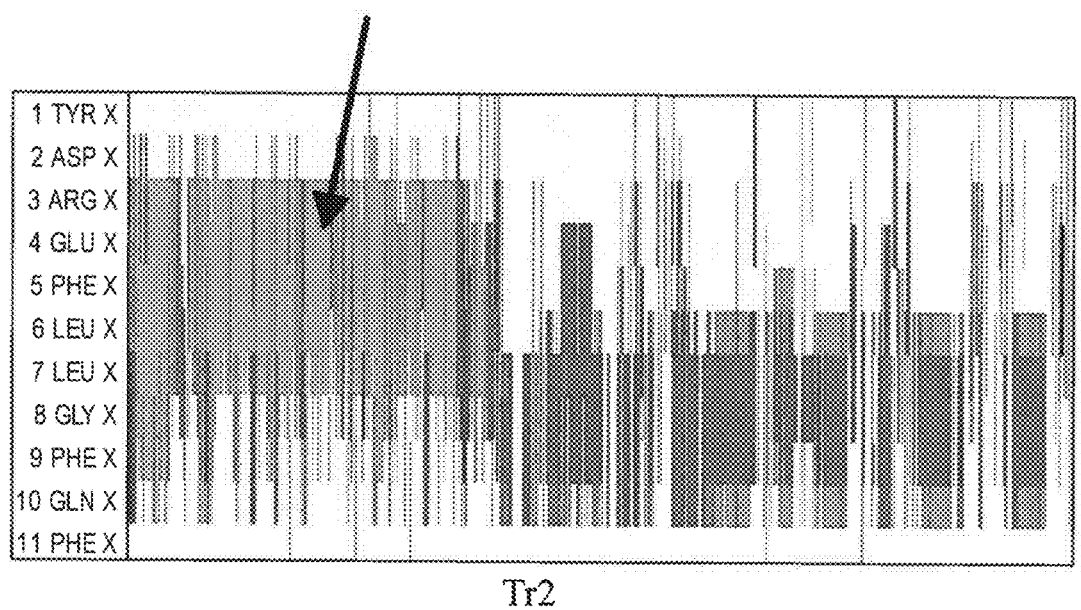
Figure 6D:
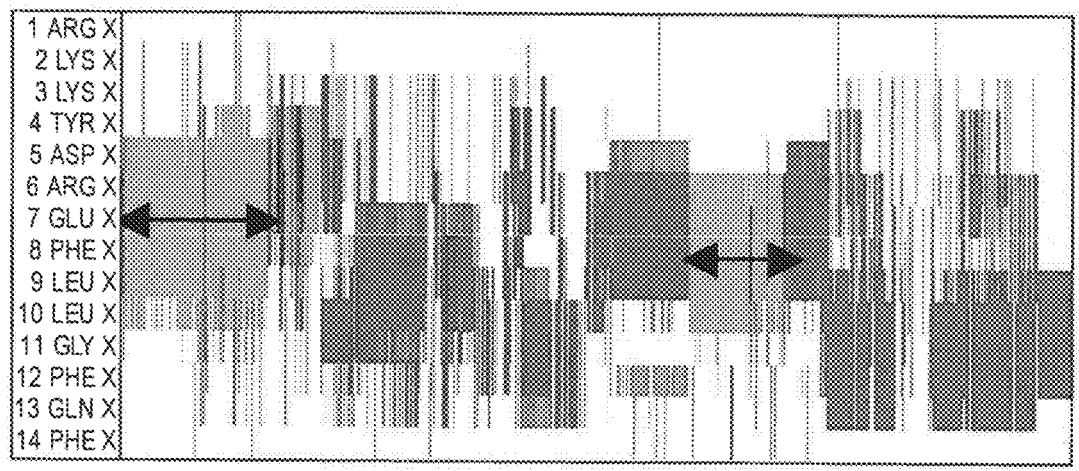

Design of Biologically Active eIF4E-Binding Peptides that Inhibit Cap-Dependent Translation The 14mer eIF4G1 peptide and its high affinity helically stabilized variant were then tested for biological activity with and without an N-terminally fused cell penetrating peptide. Ko et al reported the use of a synthesized peptide comprising residues 49 to 68 of 4EBP1 fused to the cell penetrating TAT peptide (Ko, S. Y., et al (2009) Inhibition of ovarian cancer growth by a tumor-targeting peptide that binds eukaryotic translation initiation factor 4E. *Clin Cancer Res* 15, 4336-47). They reported that it was successfully taken up by several cell lines and elicited inhibition of cap-dependent translation. This reported peptide was used as a template for the addition of the TAT peptide to the N-terminal sequences of the eIF4G1 and eIF4G1_me5 peptides. A glycine and a threonine derived from the 4E-BP1 sequence were used as a linker region between the TAT tag and the rest of the peptide sequence (see FIGS. 1A and 1B). For the peptides that were designed without the TAT tag the GT linker was retained. When these peptides are referred to in the following sections GT will be pre-appended to the relevant peptide names to indicate the presence of the linker in the absence of TAT fusion. The modified eIF4G1_me5 peptide with the GT linker was also analyzed using CD to ensure that the helix stabilization brought about by the non natural amino acids was retained (see FIGS. 4A and 4B).

To determine the efficacy of these peptides, a cell-based system to assay changes in cap-dependent translation was designed. This reporter system (termed 5'UTR_MYC_Gaussia) consists of a Gaussia luciferase gene that is designed to generate reporter mRNA that contains the 5'UTR of the c-myc mRNA, which has been reported to be under the control of cap dependent translation (De Benedetti, et al, (2004), eIF-4E expression and its role in malignancies and metastases. *Oncogene* 23, 3189-99). A reporter line derived from the MCF-7 cell line that stably expresses the 5'UTR_MYC_Gaussia reporter was generated. The robustness of this model system was determined using rapamycin, which inhibits cap-dependent translation by inhibiting mTOR from phosphorylating 4EBPs. Rapamycin inhibited cap-dependent translation (gaussia readout) in a dose-dependent manner (see FIGS. 7A to 7E and 8A to 8D).

Figure 7A:
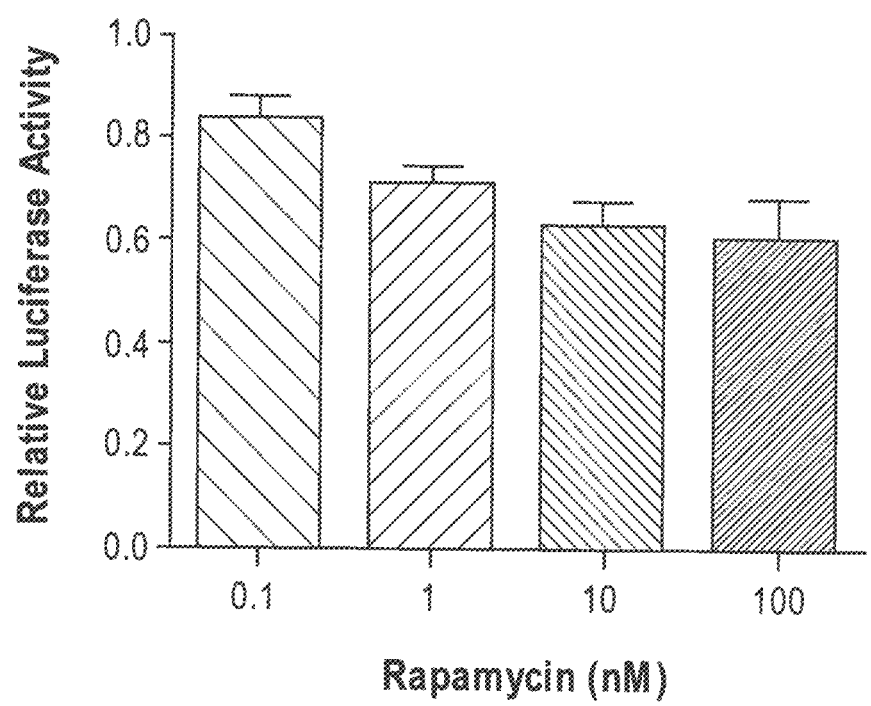
FIG. 7A shows the Rapamycin treatment of MCF-7 5'UTR_MYC_Gaussia reporter cell line to confirm robustness of cap-dependent translation assay.
Figure 8A:
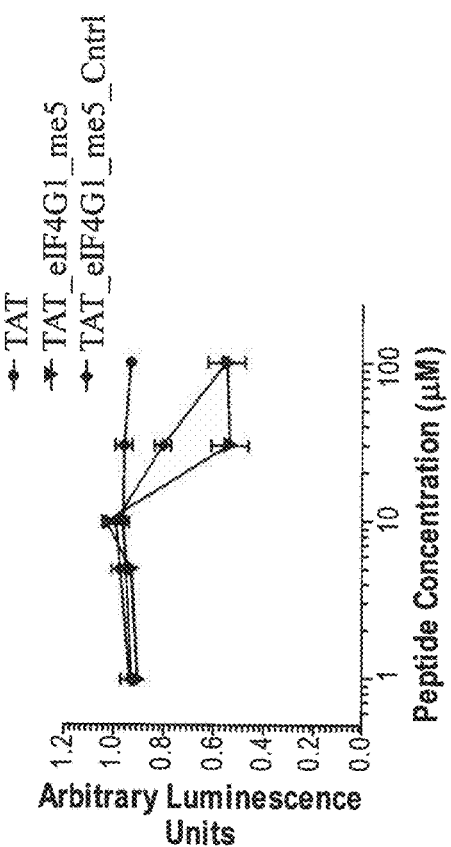
FIGS. 8A to 8D show the WST-1 assay results for MCF-7 5'UTR_MYC_Gaussia cells treated with the respective modified eIF4G1 peptides described herein.
Figure 8B:
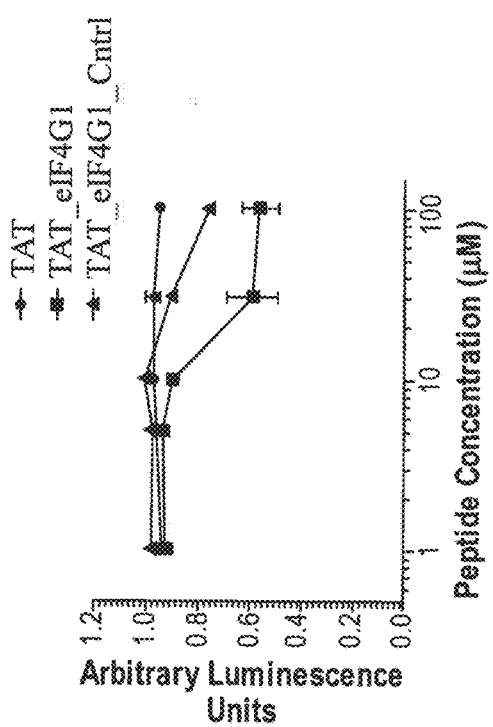
Figure 8C:
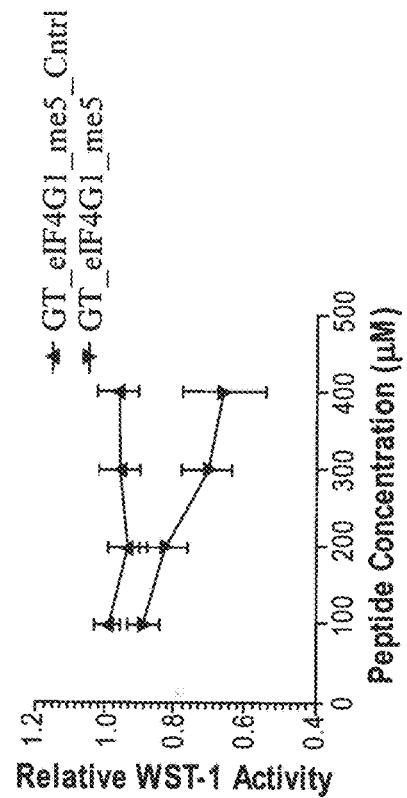
Figure 8D:
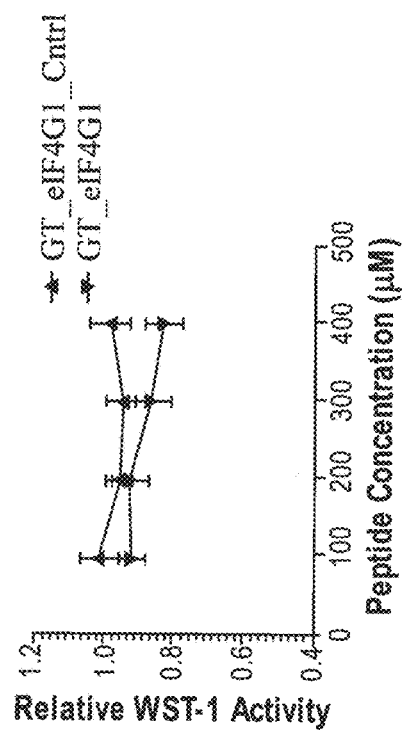

Treatment of the cell-based cap-dependent translation system with the untagged helically stabilized peptide (GT_eIF4G1_me5, SEQ ID NO: 46) showed a significant decrease in luciferase output at 400 µM (see FIG. 7E). The control peptides and the normal eIF4G1 peptide derivative showed minimal inhibition in the assay (see FIGS. 7A to 7E). The GT_eIF4G1_me5 peptide also showed some biological activity in a dose responsive manner at concentrations of 100 µM and 200 µM. In the same assay the TAT_eIF4G1 peptide (SEQ ID NO: 40) showed much stronger inhibition of cap-dependent translation and the control peptide as well showed minimal non-specific effects between 30-100 µM. The TAT_eIF4G1_me5 (SEQ ID NO: 42) also inhibited cap-dependent translation but with a very similar profile to the TAT_eIF4G1 peptide. Cap-dependent translation was not inhibited by TAT alone with only a slight decrease at 100 µM (see FIGS. 7A to 7E). These results for the tat fused peptides and the peptides without tat modification were also reflected in the corresponding WST-1 assay, a measure of cell viability, carried out 48 hours after treatment (see FIGS. 8A to 8D). The basis of the WST-1 (((4-[3-(4-iodophenyl)-2-(4-nitrophenyl)-2H-5-tetrazolio-1,3-benzene disulphonate) assay is that the stable tetrazolium salt WST-1 is cleaved to a soluble formazan by a complex cellular mechanism that occurs primarily at the cell surface. This bioreduction is largely dependent on the glycolytic production of NAD(P)H in viable cells. Therefore, the amount of formazan dye formed directly correlates to the number of metabolically active cells in the culture (Cook, J. A. & Mitchell, J. B. (1989), Viability measurements in mammalian cell systems. *Anal Biochem* 179, 1-7). In the WST-1 assay the control TAT-eIF4G1_me5 peptide (SEQ ID NO: 42), unlike the TAT_eIF4G1_Cntrl peptide (SEQ ID NO: 43), caused a significant drop in the WST-1 assay at 100 µM. However at a concentration of 30 µM there is a clear difference in the amount of inhibition caused by the TAT_eIF4G1_me5 peptide (SEQ ID NO: 42) versus the TAT_eIF4G1_me5_Cntrl peptide (SEQ ID NO: 43) in the assay.

The non TAT fused helically stabilized peptide was further studied by designing a series of peptides serially deleted at the N-terminal by a single amino acid up until the conserved Y. Each truncated peptide was acetylated as to mimic the longer chain template peptide GT_eIF4G1_me5. The cap-dependent translation and WST-1 assay revealed a sharp transition in the potency of the peptides, which is most noticeable at a peptide concentration of 400 µM (see FIGS. 15A to 15G). The GT linker region can be removed with no significant loss of activity as would be expected. However if the K621 is then removed from the positively charged region of the eIF4G1 based peptide a noticeable drop in activity is seen. The thermals shifts induced by these peptides in eIF4E were also measured and the drop from AC14 (KKRYDRE*LL5FQF) to AC13 (KRYDRE*LL5FQF) is ~2.1° C. Without wishing to be bound by theory, this drop in the affinity of the peptide for eIF4E is most probably responsible for the decrease in activity in the cell based assays. Further truncation of the peptide abolishes observable biological activity.

The Helically Stabilised eIF4G1_Me5 Peptide Increases Cell Death with or without a TAT Fusion Compared to the Unmodified eIF4G1_14mer Template Peptide.

The MCF-7 cells harboring the 5'UTR_MYC_Gaussia reporter system were treated with the GT_eIF4G1_me5 peptide (SEQ ID NO: 46) and its corresponding control peptide (GT-eIF4G1_me5_Cntrl, SEQ ID NO: 47), where the conserved motif has been mutated to alanine, to determine whether the peptide caused cell cycle arrest or/and cell death. The treated cells after 48 hours were stained with propidium iodide and the respective sub G1, G1, S and G2 populations analyzed using FACs (see FIG. 9). For the cells treated with the GT_eIF4G1_me5 peptide (SEQ ID NO: 46) there was a significant increase in the sub G1 population indicating cell death, with a slight decrease in the G2 population compared to the DMSO control. The triple ala mutant peptide control (SEQ ID NO: 47) however increased the G2 population and decreased the sub G1 population in comparison to the DMSO control. The GT-eIF4G1_me5 (SEQ ID NO: 46) also decreased the levels of cells in S phase compared to the two controls.

The above experiment was then also repeated for the TAT fused set of peptides (see FIGS. 8A to 8D and FIG. 10). FACs analysis of the PI stained treated cells revealed significant differences between the stabilized and unstabilised peptide that the WST and cap dependent translation assays did not reveal. The TAT_eIF4G1_Cntrl peptide (SEQ ID NO: 41) caused no substantive differences compared to the mock PBS treatment except a reduction in the sub G1 population and a corresponding concomitant increase in the G1 and G2 populations. The TAT_eIF4G1 peptide (SEQ ID NO: 40) causes a significant decrease in the G2 population and a large increase in the sub G1 population indicating cell death is occurring. Also the population of cells in S-phase also severely decreases. The TAT-eIF4G1_me5 (helically stabilized) peptide (SEQ ID NO 45) reduces drastically the S, G1 and G2 population with the sub G1 population encompassing 72% of all cells.

However the triple ala control for the helically stabilized peptide (TAT_eIF4G1_me5_Cntrl; SEQ ID NO: 43) also has a strong effect on the MCF-7 cells causing reduction in the G1, S and G2 populations and a large increase in the sub G1 population of ~40%. Thus the TAT_eIF4G1_me5_Cntrl peptide seems to be causing as much cell death as the eIF4G1 TAT fused peptide. Without wishing to be bound by theory, these results reveal that the helically stabilized peptide when fused to TAT is more potent than the original eIF4G1 sequence from which it is based (FIGS. 8A to 8D and FIG. 10). The strong non-specific effect seen in the TAT_eIF4G1_me5_Cntl may be the result of an increase in the interaction between the control peptide brought about by the modifications i.e. the peptide has better shape complementarity to eIF4E than the template control but key interactions have been weakened by ala replacement but not abolished. An alternative explanation is that by stabilizing the helicity of the peptide, increasing its hydrophobicity with the incorporation of the non natural amino acids A5C and AIB and removing key features involved in forming specific interaction (e.g. hydrogen bond forming potential of tyrosine) a peptide is being generated with a much higher potential for promiscuous/non specific binding.

The TAT Fused eIF4G1 Derivative Peptides Decrease Levels of Endogenous c-Myc and Induce Cell Death by Apoptosis.

Figure 11:
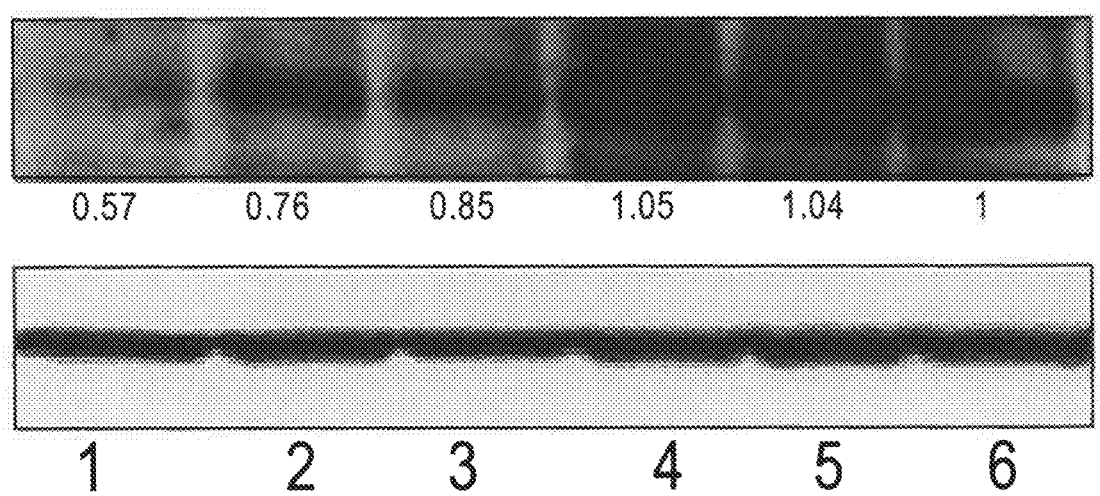
FIG. 11 shows the Western blot of endogenous c-myc levels in MCF-7 cells after 48 hour treatment with the modified eIF4G1 peptides described herein at a concentration of 15 µM. Lane 1: TAT_eIF4G1_me5 (SEQ ID NO: 42), Lane 2: TAT_eIF4G1_me5_Cntrl (SEQ ID NO: 43), Lane 3: TAT_eIF4G1 (SEQ ID NO: 40), Lane 4: TAT_eIF4G1_Cntrl (SEQ ID NO: 41), Lane 5: TAT (SEQ ID NO: 7) and Lane 6 is a PBS MOCK treatment. Bottom panel shows actin loading control. The western blot of endogenous c-myc was repeated independently twice. A representative western blot is shown with values corresponding to the fold change in comparison to the PBS mock treatment and normalized to actin for visualization.

To investigate further the effects of eIF4G1 derivative peptides on MCF-7 cells the expression levels of endogenous c-myc were blotted for and the cells were also stained for annexin. Only the TAT fused peptides were used in these experiments due to their higher potency as observed in the WST-1 assay and the cell based cap dependent translation assay. The MCF-7 cells were treated with 15 µM peptide for 6 hours after serum starvation overnight in an identical manner to the cap-dependent translation assay (see FIG. 11). The amount of c-myc expressed after 6 hours when treated with either PBS (Lane 6), the TAT peptide (Lane 5) or the TAT_eIF4G1_Cntrl peptide (Lane 4) were identical. Treatment with TAT_eIF4G1 (Lane 3) resulted in a marked decrease in endogenous c-myc expression. However MCF-7 cells after exposure to the TAT_eIF4G1_me5_Cntrl peptide (Lane 2) had a similar reduction in c-myc protein levels in comparison to TAT_eIF4G1 (Lane 3). Reduction in c-myc expression is most pronounced when the MCF-7 cells are treated with the TAT_eIF4G1_me5 (Lane 1). The same peptide treatments were again carried out again but with the peptides at a concentration of 30 µM and annexin staining analyzed after 48 hours of treatment (see FIGS. 12A to 12F). The PBS mock (FIG. 12A), the TAT peptide (FIG. 12B) and TAT_eIF4G1_Cntrl peptide treatments (FIG. 12C) produced few cells that could be stained. The cells treated with TAT_eIF4G1 (FIG. 12D) and TAT_eIF4G1_me5 (FIG. 12F) caused a high proportion of the cells to stain with annexin indicating that apoptosis was occurring. Interestingly the TAT_eIF4G1_me5_Cntrl peptide treatment, which caused a reduction in c-myc expression in the same region as the TAT_eIF4G1, causes some annexin staining but significantly at much lower levels that TAT_eIF4G1. Without wishing to be bound by theory, this result may indicate that the effects seen in MCF-7 cells, induced by the control peptide, are not working via an identical pathway to the TAT_eIF4G1 peptide, considering that it caused a similar increase in the sub G1 population in the PI staining experiments. Such an interpretation would support the hypothesis that the modifications in the control peptide maybe increasing its ability to bind non-specifically.

The Cell Penetrating Peptide TAT Enhances Peptide Binding to eIF4E.

To ascertain the reason for the peptides TAT_eIF4G1 (SEQ ID NO: 43) and TAT_eIF4G1_me5 (SEQ ID NO: 42) possessing similar activities in the MCF-7 5'UTR_MYC_Gaussia reporter cell line they were further characterized biophysically. Both peptides and their controls were initially screened using the fluorescence based thermal stability assay and in contrast to the eIF4G1 peptide alone the TAT_eIF4G1 peptide produces a thermal shift that is ~2.70° C. larger. An improvement of a similar magnitude however is not seen for the TAT_eIF4E_me5 peptide however it still induces a greater thermal shift in the $T_m$ of eIF4E than the TAT_eIF4GI peptide of ~0.82° C. The apparent $K_d$s for the peptides TAT_eIF4G1-me5 and TAT_eIF4GI were then determined by ITC to be 10.17±2.55 nM and 56.18±8.60 nM. This revealed that the eIF4GI peptide when fused to TAT had a $K_d$ that was ~2.7-fold lower than that of the shorter parent peptide. The $K_d$ for the non-TAT tagged helically stabilized peptide is approximately the same. Without wishing to be bound by theory, the improvement in $K_d$ of the TAT_eIF4G1 in comparison to the non TAT fused template explains why only the use of more sensitive techniques such as FACS analysis and western blotting discerned differences in the biological action of the modified peptide.

Figure 14:
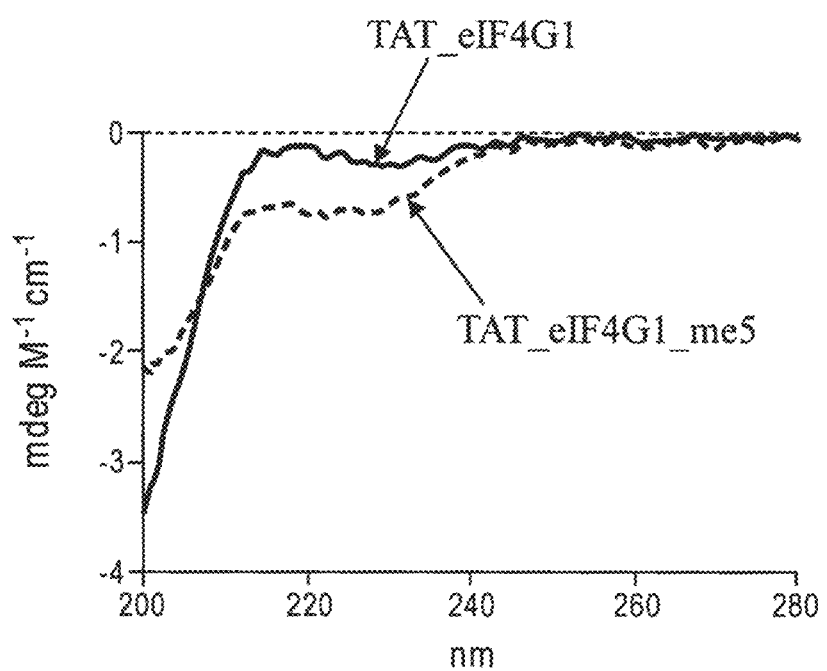
FIG. 14 shows the far-UV CD spectra for TAT_eIF4G1_me5 (SEQ ID NO: 42) and TAT_eIF4G1 (SEQ ID NO: 40). TAT_eIF4G1 shows a spectrum typical of random coil secondary structure whilst TAT_eIF4G1_me5 shows the development of a shoulder at 220 nm indicating partial helical character.
Figure 15E:
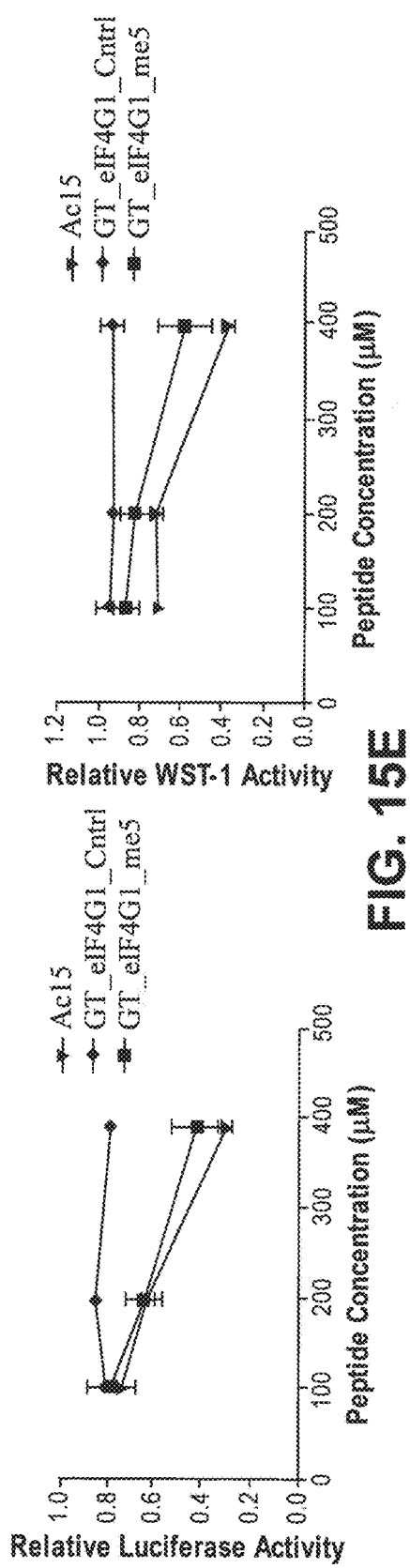
Figure 15F:
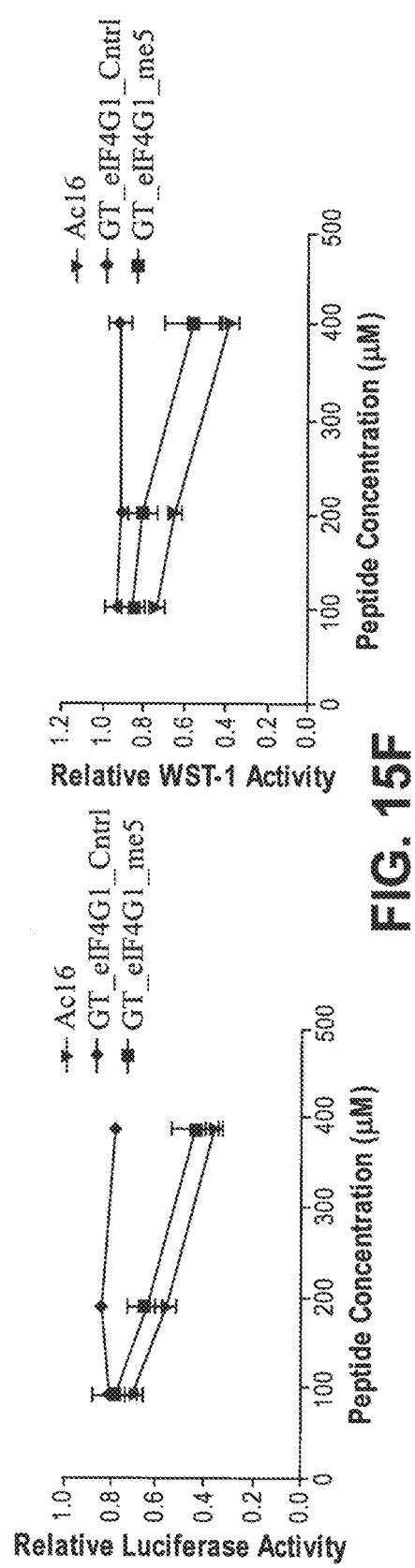
Figure 16:
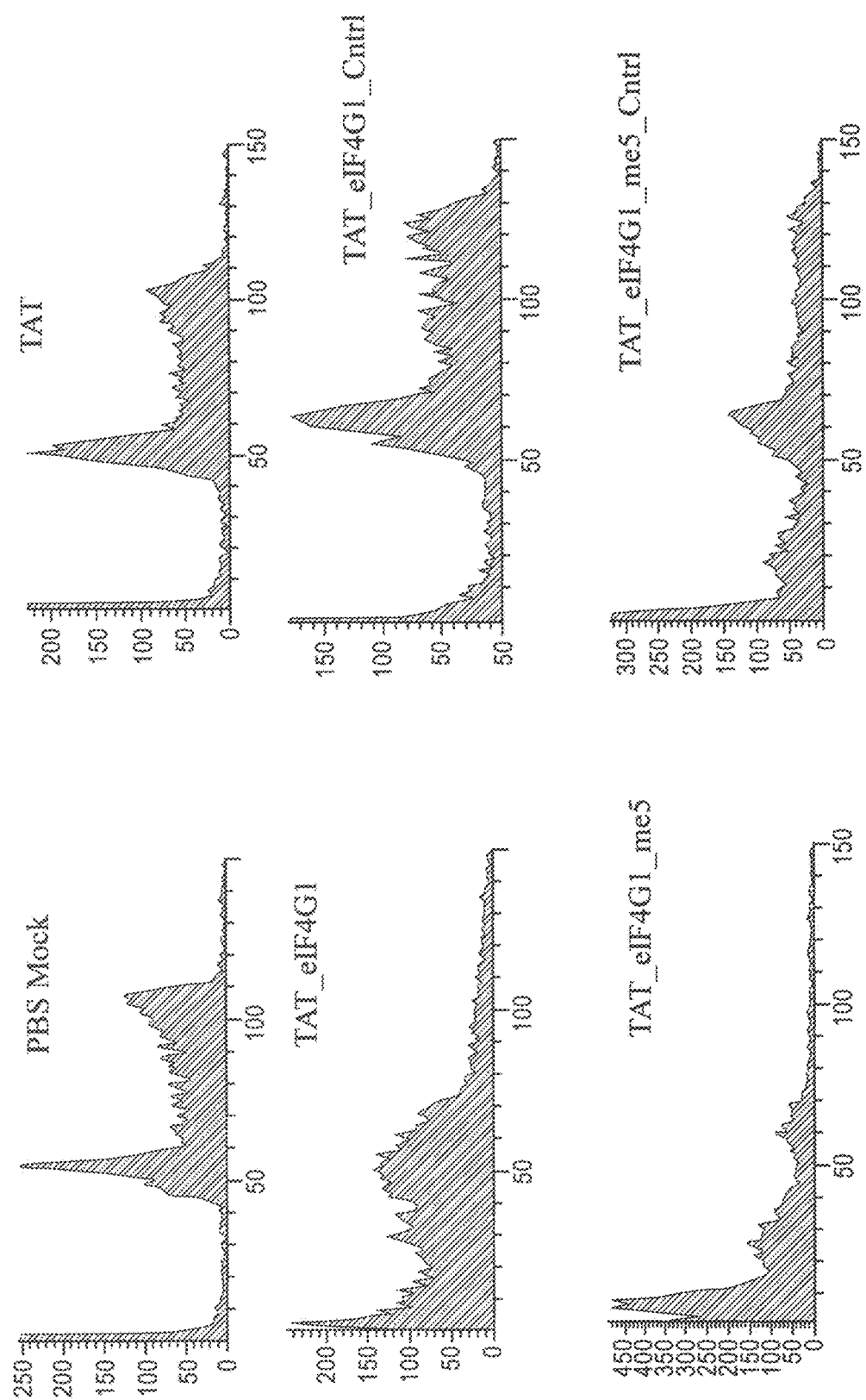
FIG. 16 shows the FACS analysis histograms showing PI-staining of MCF-7 based reporter cells treated with the water soluble TAT fused modified eIF4G1 peptides at 30 μM.

Temperature shifts revealed no binding for the TAT tag by itself and examination of the eIF4E surface N-terminal to the peptide revealed no obvious potential interactions in the eIF4E-eIF4G1 peptide crystal structure. Therefore it was hypothesized that by increasing the length of the peptide the probability that the correct conformation occurs increases and in doing so results in a lower $K_d$. The CD spectra for TAT_eIF4G1-me5 and TAT_eIF4G1 peptides were recorded and revealed elements of secondary structure for both (see FIG. 14). The CD spectrum for TAT_eIF4G1 is predominately random coil whilst the spectrum for TAT_eIF4G1_me5 clearly shows a shoulder at 220 nm that indicates helical formation within the peptide. Computer simulations using the methods applied to the shorter eIF4G1 based peptides could not be extended to the TAT tagged peptides due to their greater length. As with the case of the non tagged peptides the non-modified TAT_eIF4G1 peptide has a much less favourable enthalpy than the helically stabilized TAT_eIF4G1_me5 peptide. However in contrast to all the other stabilized peptides it has a favourable entropy of 15 cal mol$^{-1}$.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXAMPLES

Example 1

Materials and Methods

The peptides Tr2_AIB1 to 4, Tr2_AIB3_ALA, Tr2_AIB3_A3C to A5C, Tr2_Ala_A5C1 to Tr2_Ala_A5C5, Tr2_me5_1 to Tr2_me5_3, eIF4G1_me5 and the TAT fused peptides described in FIG. 1B were all synthesized by $1^{st}$ Base, Singapore with greater than 90% purity. All other peptides were synthesized as described below.

Example 2

Reagents and Peptide Synthesis

All Fmoc amino acids (AA) were obtained from Novabiochem and contained the following side chain protecting groups: Asn(Trt), Asp(OtBu), Arg(Pbf), Gln(Trt), Glu(OtBu), Lys(Boc) and Tyr(tBu). N-[(1H-Benzotriazol-1-yl)(dimethylamino)methylene]-N-methylmethanaminium hexafluorophosphate N-oxide (HBTU), N-hydroxybenzotriazole (HOBt), and Rink amide MBHA resin were also obtained from Novabiochem. Diisopropylethylamine (DIPEA), piperidine, trifluoroacetic acid (TFA), N-methylpyrrolidone (NMP), triisopropylsilane (TIS), anhydrous ethyl ether were obtained from Sigma Aldrich. Dichloromethane (DCM), N,N-Dimethylformamide (DMF) and HPLC gradient grade acetonitrile were obtained from Merck.

Peptides were synthesized using a CEM Liberty automated microwave peptide synthesizer on Rink amide MBHA resin. Fmoc deprotection was performed using 20% piperidine in DMF at 75° C. for 5 minutes at 40 W. Amino acid coupling reactions were performed in 5-fold molar excess of Fmoc-protected amino acids dissolved in DMF with activating reagents HBTU:HOBt:DIPEA:amino acid (0.9:1:2:1 equivalents). Coupling reactions were conducted over 10 minutes at 40 W at 75° C. Cleavage was performed using 5 ml of cleavage solution TFA:water:TIS (95:2.5:2.5 v/v) for 30 min at 40° C. Filtration was carried out and the resin was washed with DCM thrice to obtain the filtrate. The filtrate was concentrated under centrifugal evaporation and the crude peptides were precipitated using ice-cold anhydrous diethyl ether. HPLC purification of peptide was performed using a Waters X-bridge C18 column (3 μm, 19×150 mm) at 215 nm wavelength. Separation was achieved by gradient elution of 25-45% solvent B (solvent A=0.1% TFA in water; solvent B=0.1% TFA in acetonitrile) at a flow rate of 5 ml/min. Molecular mass analysis was performed using a ABI Mariner Mass Spectrometer with electrospray ionization.

Example 3

Protein Expression and Purification

Full length human eIF4E was expressed and purified as described in Brown, C. J., et al, (2007), Crystallographic and mass spectrometric characterisation of eIF4E with N7-alkylated cap derivatives. *J Mol Biol* 372, 7-15.

Example 4

Thermal Stability Measurements

A fluorescence based thermal shift assay was used to screen and rank the rationally designed eIF4E binding derivative peptides. The fluorescent dye Sypro Red was used to monitor thermal denaturation of eIF4E. Binding of the dye molecule to eIF4E, as it unfolds due to thermal denaturation, results in a sharp increase in the fluorescence intensity. The midpoint of this transition is termed the $T_m$. The thermal shift assay was conducted in the iCycler Real Time Detection System (Bio-Rad, Hercules, Calif.). The system contains a heating/cooling device for accurate temperature control and a charge-coupled device (CCD) detector for simultaneous imaging of the fluorescence changes in the wells of the microplate. Protein samples studied were made up to a total volume of 50 μl in PBS (Phosphate Buffered Saline, 2.7 mM KCL and 137 mM NaCl, pH 7.4) with Sypro Red, (Invitrogen, 5000×DMSO stock) at a 3.125× concentration. The final protein concentration was 10 μM. Protein samples were incubated with derivative peptides at a concentration of a 100 μM. The plate was heated from 20 to 90° C. with a heating rate of 1° C./min. The fluorescence intensity was measured with Ex/Em: 575/635 nm.

The fluorescence imaging data from the CCD detector were fitted to Eq. (1) (see also Lo, M. C., et al (2004). Evaluation of fluorescence-based thermal shift assays for hit identification in drug discovery. *Anal Biochem* 332, 153-9) to obtain $\Delta H_u$, $\Delta C_{pu}$, and $T_m$ by nonlinear regression using the program Prism 4.0, Graphpad:

$$F_t = F_{post} + \frac{(F_{pre} - F_{post})}{1 + \exp\left\{\frac{-\Delta H_u}{R}\left(\frac{1}{T} - \frac{1}{T_m}\right) + \frac{\Delta C_{pu}}{R}\left[\ln\left(\frac{T}{T_m}\right) + \frac{T_m}{T} - 1\right]\right\}} \quad (1)$$

where $F_t$ is the fluorescence intensity at temperature T; $T_m$ is the midpoint temperature of the protein-unfolding transition, $F_{pre}$ and $F_{post}$ are the pretransitional and posttransitional fluorescence intensities, respectively, R is the gas constant, $\Delta H_u$ is the enthalpy of protein unfolding, and $\Delta C_{pu}$ is the heat capacity change on protein unfolding. In the absence of ligand, $T_m=T_0$, $\Delta C_{pu}=\Delta C^{T0}_{pu}$, and $\Delta H_u=\Delta H^{T0}_u$.

To calculate the ligand-binding affinity at $T_m$ for the derivative eIF4E binding peptides, Eq. (2) was used:

$$K_{L(T_M)} = \frac{\exp\left(\frac{-\Delta H^{T_o}_u}{R}(1/T_m - 1/T_o) + \Delta C^{T_o}_{pu}\left[\ln\left(\frac{T_m}{T_o}\right) + \frac{T_o}{T_m} - 1\right]\right)}{[L_{T_m}]} \quad (2)$$

To compare binding affinities for the derivative peptides to eIF4E calculated from the thermal shift data, the binding affinity at temperature T ($K_{L(T)}$) must be calculated. $K_{L(T)}$ can be calculated from $K_{L(Tm)}$ using Eq. (3A):

$$K_{L(T)} = K_{L(T_m)}\exp\left(\frac{-\Delta H_{L(T)}}{R}\left(\frac{1}{T} - \frac{1}{T_m}\right)\right) \quad (3A)$$

where $K_{L(T)}$ is the ligand association constant at temperature T, and $\Delta H_{L(T)}$ is the van't Hoff enthalpy of binding at temperature T. The value of $\Delta H_{L(T)}$ was taken to be 5 kcal/mol.

Example 4

Circular Dichroism Studies

CD was measured on a JASCO J-810 spectropolarimeter and spectra were recorded in a 1 cm quartz cuvette (Helmer) in 5 mM sodium phosphate buffer (pH 7.0). Far UV CD spectra were recorded from 260 to 200 nm at a peptide concentration of 2.5 µM. The CD signal was converted to Delta Epsilons (Δε). CD spectra were recorded at a data pitch of 0.2 nm at 50 nm/min, a response time of 2 s and the bandwidth set at 2 nm.

Example 5

Isothermal Titration Calorimetry (ITC)

The binding affinities and binding enthalpies of the modified eIF4G1 peptides as described herein to eIF4E were measured by ITC. ITC experiments were conducted in a VP-ITC Unit (MicroCal, Northampton, Mass.). In a typical ITC experiment, either 10 µM of eIF4E was loaded into the cell with either 100 or 200 µM of a modified eIF4G1 peptide described herein in the titrating syringe. eIF4E was dialysed into Phosphate Buffered Saline (2.7 mM KCl and 137 mM NaCl, pH 7.4). All peptides used were weighed out as solids and dissolved in DMSO to a concentration of 10 mM or in the case of the TAT-containing modified eIF4G1 peptides the dialysis buffer. The buffer used for dialysis of the protein was used to dilute the peptides to their final working concentration. The protein buffer solution was matched to the peptide solution by the addition of DMSO in the case of the non TAT fused peptides. The titration experiments were performed at 20° C. with an initial 2 µl injection with duration of 4 s, fooled by 28 10 µl injections with a duration of 7.1 s. The spacing between each injection was 150 s. The stirring speed during the titration was 290 rpm. Data was analyzed using Microcal Origin software by fitting to a single-site binding model. Correction for the enthalpy of ligand dilution was carried out by subtracting a linear fit from the last three data points of the titration, after the interaction had reached saturation.

Example 6

Computer Simulations

To examine the conformational spectrum of the eIF4G1 peptides and the modified eIF4G1 peptides described herein, their folding was simulated using molecular dynamics simulations. The structural models of the linear peptides were constructed and using the XLEAP module of AMBER9 (Case, D. A., et al., (2005) The Amber biomolecular simulation programs. *J Comput Chem* 26, 1668-88). Parameters for the non-natural amino acids, 1-aminocyclopentanecarboxylic acid and $C_\alpha$-Me-L-Phenylalanine were built using the Antechamber[28] module of AMBER9 (Wang, J., et. al, (2006) Automatic atom type and bond type perception in molecular mechanical calculations. *J Mol Graph Model* 25, 247-6). MD simulations were carried out using the Generalized Born implicit solvent method (GB) that has been shown to be successful in simulating peptide folding patterns (Shell, M. S., et al, (2008) A test on peptide stability of AMBER force fields with implicit solvation. *J Phys Chem B* 112, 6878-86). The major advantage of this method over using explicit solvent is faster and larger sampling which the folding patterns of small peptides to be studied easily. The force field ff96 was used along with the Onufriev, Bashford and Case model (incorporated in AMBER9 under the option igb=5) (Onufriev, A., et al, (2004). Exploring protein native states and large-scale conformational changes with a modified generalized born model. *Proteins* 55, 383-94) for optimal Born radii for macromolecules. A salt concentration of 0.2 mM was used. Hydrogen containing bonds were constrained using SHAKE (Van Gunsteren, W. F. & Berendsen, H. J. C. (1977) Algorithms for macromolecular dynamics and constraint dynamics. *Molecular Physics* 34, 1311-1327). After initial minimizations, the system was gradually heated to 325K, equilibrated for 100 ps and finally production runs were carried out for 200 ns on each of the 4 peptides. A temperature of 325K was used to enhance the sampling to enable the exploration of larger regions of conformational space. PyMOL and Visual Molecular Dynamics[34] (VMD) were used for visualization and analysis (Humphrey, W., et al, (1996) VMD: visual molecular dynamics. *J Mol Graph* 14, 33-8, 27-8).

Example 7

Construction of Cap-Dependent Translation Reporter Construct

The c-myc 5'UTR was amplified from MCF-7 genomic DNA, isolated using a Qiagen DNeasy tissue kit, using the primers Cmyc_For and Cmyc_Rev. The PCR product was gel purified and reamplified using the primers Cmyc_For_nested and Cmyc_Rev_nested. The CMV promoter was isolated from pCDNA3 (Invitrogen) using the primers CMV_For and CMV_Reverse. The gaussia luciferase gene was isolated from the pNEBR-X1GLuc plasmid (NEB) using the primers Gaussia_For and Gaussia_Rev. The IRES eGFP sequence was isolated from a pLENTI6 plasmid derivative containing the ECMV IRES fused to eGFP, which was a gift from Dr P Mueller, with the primers IRES_eGFP_For snd IRES_eGFP_Rev. All the resulting PCR products were gel purified using standard techniques. Primers were designed to ensure that the 3' end of the CMV amplified region overlapped with the 5' end of the c-myc UTR region, that the 3' end of the c-myc region overlapped with the 5' end of the gaussia luciferase gene and that the 3' end of the gaussia gene overlapped with the 5' end of the IRES eGFP sequence. All overlapping regions were greater than 18 bp in length. Equimolar amounts of each isolated PCR product was placed into a 50 ul PCR reaction and amplified with the primers Biscistronic_nested_For and Biscistronic_nested_Rev to generate the linear eIF4E reporter construct. A band of the expected length 2.8 kb was then gel purified. The PCR was then reamplified with the following Gateway (Invitrogen) compatible primers (BIS_GAT_F, Bis_GAT_R, attB1 and attB2) in two separate PCR reactions with the intermediate PCR product gel purified. The resulting gateway compatible linear PCR product was then recombined using BP Clonase™ II into pDONR221 (Invitrogen). After recombination the resulting construct was digested with the restriction enzymes NDE1 and BAMH1, and ligated into NDE1 and BAMH1 digested pCDNA3 vector for mammalian expression (Invitrogen). This construct was termed the 5'UTR_MYC_Gaussia vector. All PCR reactions were carried out with Herculase II Fusion DNA Polymerase. The 5'UTR_MYC_Gaussia reporter cell line was generated by transfecting MCF-7 cells with the 5'UTR_MYC_Gaussia plasmid using LIPOFECTAMINE reagent (Invitrogen) and selecting stably transfected clones using G418 (1000 µg/mL) (Invitrogen).

Example 8

Cap-Dependent Translation Cell-Based Assay

MCF-7 (5'UTR_MYC_Gaussia) cells were cultured in DMEM with 10% FCS. Twenty thousand cells were then seeded per well in 48-wells plates in DMEM serum-free media overnight at 37° C. Before overnight incubation, cells were incubated at room temperature for 30 mins. Cells were then cultured in media containing 10% FCS with Rapamycin for 24 hrs and at concentrations of 100 nM, 10 nM, 1 nM, 0.1 nM. Gaussia-Luc activities in cells were measured using Gaussia Luciferase Assay Kit (NEB) with SpectraMax M5 (molecular Devices). Cells were also cultured with the modified eIF4G1 peptides described herein for 6 hours at concentrations of 1 µM, 5 µM, 10 µM, 30 µM, 100 µM, 200 µM, 300 µM and 400 µM including a 1% DMSO and PBS mock treatment as well. Only the non-TAT containing peptides were screened at the final three concentrations.

Example 9

WST-1 Assay

MCF-7 (5'UTR_MYC_Gaussia) cells were cultured in DMEM with 10% FCS. Twenty thousand cells were then seeded per well in 48-wells plates in DMEM serum-free media overnight at 37° C. Before overnight incubation, cells were incubated at room temperature for 30 mins. After overnight incubation cells were then cultured in media containing 10% FCS with the modified eIF4G1 peptides described herein for 6 hours at concentrations of 1 µM, 5 µM, 10 µM, 30 µM, 100 µM, 200 µM, 300 µM and 400 µM including a 1% DMSO and PBS mock treatment as well. After 48 hrs of treatment, MCF-7 cells were incubated with Cell Proliferation Reagent WST-1(Roche) for 30 mins at 37° C. Absorbances of cell media were then read at 450 nm with SpectraMax M5.

Example 10

Propidium Iodide Staining and FACS Analysis

MCF-7 (5'UTR_MYC_Gaussia) cells were cultured in DMEM with 10% FCS. Two hundred fifty thousand cells were then seeded per well in 6-wells plates containing DMEM serum-free media overnight at 37° C. Before overnight incubation, cells were incubated at room temperature for 30 mins. After incubation overnight the cells were cultured in media containing 10% FCS with the non TAT containing modified eIF4G1 peptides and their corresponding control peptides for 48 hrs and at a concentration of 400 µM. TAT fused modified eIF4G1 peptide treatments were carried out at 30 µM. A 1% DMSO and a PBS mock treatment was also carried out. Cells were harvested and fixed in 65% ethanol in PBS and incubated at 4° C. for 2 hrs. Cells were spun down and resuspended with Propidium iodide staining solution containing Rnase A. Cells were analyzed using LSR II (BD).

Example 11

Annexin IV Assay

MCF-7 cells were cultured in DMEM with 10% FCS. Two hundred fifty thousand cells were then seeded per well in 6-wells plates containing DMEM serum-free media overnight at 37° C. Before overnight incubation, cells were incubated at room temperature for 30 mins. Cells were then cultured in media containing 10% FCS with the TAT fused modified eIF4G1 peptides and their controls for 48 hrs and at a concentration of 30 uM. A mock PBS treatment was also included. Cells were harvested, washed in PBS and spun down at 200 g for 5 mins. Cell pellets were resuspended in Annexin-VFLUOS labeling solution from Roche and incubated for 10-15 min at 15-25° C. Cells were then analyzed using LSR II (BD).

Example 12

Western Blotting

MCF-7 cells were cultured in DMEM with 10% FCS. Three hundred fifty thousand MCF-7 cells were then seeded per well in 6-wells plates containing DMEM serum-free media overnight at 37° C. Before overnight incubation, cells were incubated at room temperature for 30 mins. After the overnight incubation cells were then cultured in media containing 10% FCS with the TAT fused modified eIF4G1 peptides and their respective controls at a concentration of 30 uM. A mock PBS treatment was also included. Cells were harvested at 6 hrs and lysed in RIPA buffer. Protein concentration was determined using a Lowry Assay kit (Biorad). Samples were loaded at 30 ug and blotted against monoclonal antibody c-myc (Sigma Aldrich #M4439). B-actin was blotted for as a loading control.

Statistical Analysis

Data were analyzed using Prism software (Graphpad Inc.). Statistical significance of differences in cell viability and luciferase activity was calculated by non paired Student's t-test. All statistical tests were two-sided. $P<0.05$ was considered to be statistically significant.

What is claimed is:

1. A method of inhibiting eukaryotic translation initiation factor 4E (eIF4E) by administering of a pharmaceutically effective amount of a modified eukaryotic translation initiation factor 4 gamma 1 (eIF4G1) peptide, wherein the peptide has been modified to stabilize the α-helix, wherein the peptide comprises:
   (a) the amino acid sequence KKRYDREFLL*FQF (SEQ ID NO:10); or
   (b) the amino acid sequence KKRYDRE*LL*FQF (SEQ ID NO:2),
wherein * represents a non-natural amino acid.

2. The method of claim 1, wherein the peptide comprises the amino acid sequence KKRYDRE*LL5FQF (SEQ ID NO:6), wherein * represents a non-natural amino acid and 5 represents 1-aminocyclopentanoic acid.

3. A method for the treatment of autism and cancer, comprising administering a pharmaceutically effective amount of a modified eukaryotic translation initiation factor 4 gamma 1 (eIF4G1) peptide, wherein the peptide has been modified to stabilize the α-helix, wherein the peptide comprises:
   (a) the amino acid sequence KKRYDREFLL*FQF (SEQ ID NO:10); or
   (b) the amino acid sequence KKRYDRE*LL*FQF (SEQ ID NO:2),
wherein * represents a non-natural amino acid.

4. The method of claim 3, wherein the cancer is selected from the group consisting of breast cancer, lung cancer, head and neck cancer, esophagus cancer, skin cancer, bladder cancer, colon cancer, cervix cancer and prostate cancer.

5. The method of claim 3, wherein the peptide comprises the amino acid sequence KKRYDRE*LL5FQF (SEQ ID NO:6), wherein * represents a non-natural amino acid and 5 represents 1-aminocyclopentanoic acid.

* * * * *

SEQUENCE LISTING

<160> NUMBER OF SEQ ID NOS: 51

<210> SEQ ID NO 1
<211> LENGTH: 14
<212> TYPE: PRT
<213> ORGANISM: Artificial
<220> FEATURE:
<223> OTHER INFORMATION: Designed peptide based on eIF4G1 peptide
<220> FEATURE:
<221> NAME/KEY: misc_feature
<222> LOCATION: (2)..(5)
<223> OTHER INFORMATION: Xaa can be any kind of amino acid known in the
      art
<220> FEATURE:
<221> NAME/KEY: misc_feature
<222> LOCATION: (8)..(11)
<223> OTHER INFORMATION: Xaa can be any kind of amino acid known in the
      art

<400> SEQUENCE: 1

Lys Xaa Xaa Xaa Xaa Arg Glu Xaa Xaa Xaa Xaa Phe Gln Phe
1               5                   10

<210> SEQ ID NO 2
<211> LENGTH: 14
<212> TYPE: PRT
<213> ORGANISM: Artificial
<220> FEATURE:
<223> OTHER INFORMATION: Designed peptide based on eIF4G1 peptide
<220> FEATURE:
<221> NAME/KEY: misc_feature
<222> LOCATION: (8)..(8)
<223> OTHER INFORMATION: Xaa can be any kind of amino acid known in the
      art
<220> FEATURE:
<221> NAME/KEY: misc_feature
<222> LOCATION: (11)..(11)
<223> OTHER INFORMATION: Xaa can be any kind of amino acid known in the
      art

<400> SEQUENCE: 2

Lys Lys Arg Tyr Asp Arg Glu Xaa Leu Leu Xaa Phe Gln Phe
1               5                   10

<210> SEQ ID NO 3
<211> LENGTH: 14
<212> TYPE: PRT
<213> ORGANISM: Artificial
<220> FEATURE:
<223> OTHER INFORMATION: Designed peptide based on eIF4G1 peptide
<220> FEATURE:
<221> NAME/KEY: misc_feature
<222> LOCATION: (4)..(4)
<223> OTHER INFORMATION: Xaa can be any kind of amino acid known in the
      art
<220> FEATURE:
<221> NAME/KEY: misc_feature
<222> LOCATION: (8)..(9)
<223> OTHER INFORMATION: Xaa can be any kind of amino acid known in the
      art
<220> FEATURE:
<221> NAME/KEY: misc_feature
<222> LOCATION: (12)..(12)
<223> OTHER INFORMATION: Xaa can be any kind of amino acid known in the
      art

<400> SEQUENCE: 3

Lys Lys Arg Xaa Asp Arg Glu Xaa Xaa Leu Gly Xaa Gln Phe
1               5                   10

<210> SEQ ID NO 4
<211> LENGTH: 14

```
<212> TYPE: PRT
<213> ORGANISM: Artificial
<220> FEATURE:
<223> OTHER INFORMATION: Designed peptide based on eIF4G1 peptide
<220> FEATURE:
<221> NAME/KEY: misc_feature
<222> LOCATION: (8)..(8)
<223> OTHER INFORMATION: Xaa can be any kind of amino acid known in the
      art

<400> SEQUENCE: 4

Lys Lys Arg Tyr Asp Arg Glu Xaa Leu Leu Gly Phe Gln Phe
1               5                   10

<210> SEQ ID NO 5
<211> LENGTH: 11
<212> TYPE: PRT
<213> ORGANISM: Artificial
<220> FEATURE:
<223> OTHER INFORMATION: Designed peptide based on eIF4G1 peptide
<220> FEATURE:
<221> NAME/KEY: misc_feature
<222> LOCATION: (5)..(5)
<223> OTHER INFORMATION: Xaa can be any kind of amino acid known in the
      art
<220> FEATURE:
<221> NAME/KEY: misc_feature
<222> LOCATION: (8)..(8)
<223> OTHER INFORMATION: Xaa is 1-amino cyclopentanoic acid

<400> SEQUENCE: 5

Tyr Asp Arg Glu Xaa Leu Leu Xaa Phe Gln Phe
1               5                   10

<210> SEQ ID NO 6
<211> LENGTH: 14
<212> TYPE: PRT
<213> ORGANISM: Artificial
<220> FEATURE:
<223> OTHER INFORMATION: Designed peptide based on eIF4G1 peptide
<220> FEATURE:
<221> NAME/KEY: misc_feature
<222> LOCATION: (8)..(8)
<223> OTHER INFORMATION: Xaa can be any kind of amino acid known in the
      art
<220> FEATURE:
<221> NAME/KEY: misc_feature
<222> LOCATION: (11)..(11)
<223> OTHER INFORMATION: Xaa is 1-amino cyclopentanoic acid

<400> SEQUENCE: 6

Lys Lys Arg Tyr Asp Arg Glu Xaa Leu Leu Xaa Phe Gln Phe
1               5                   10

<210> SEQ ID NO 7
<211> LENGTH: 11
<212> TYPE: PRT
<213> ORGANISM: Artificial
<220> FEATURE:
<223> OTHER INFORMATION: TAT

<400> SEQUENCE: 7

Tyr Gly Arg Lys Lys Arg Arg Gln Arg Arg Arg
1               5                   10

<210> SEQ ID NO 8
<211> LENGTH: 14
<212> TYPE: PRT
<213> ORGANISM: Homo sapiens

<400> SEQUENCE: 8
```

Lys Lys Arg Tyr Asp Arg Glu Phe Leu Leu Gly Phe Gln Phe
1               5                   10

<210> SEQ ID NO 9
<211> LENGTH: 14
<212> TYPE: PRT
<213> ORGANISM: Artificial
<220> FEATURE:
<223> OTHER INFORMATION: Designed peptide based on eIF4G1 peptide
<220> FEATURE:
<221> NAME/KEY: misc_feature
<222> LOCATION: (8)..(8)
<223> OTHER INFORMATION: Xaa can be any kind of amino acid known in the art
<220> FEATURE:
<221> NAME/KEY: misc_feature
<222> LOCATION: (11)..(11)
<223> OTHER INFORMATION: Xaa can be any kind of amino acid known in the art

<400> SEQUENCE: 9

Lys Lys Arg Tyr Asp Arg Glu Xaa Leu Leu Xaa Phe Gln Phe
1               5                   10

<210> SEQ ID NO 10
<211> LENGTH: 14
<212> TYPE: PRT
<213> ORGANISM: Artificial
<220> FEATURE:
<223> OTHER INFORMATION: Designed peptide based on eIF4G1 peptide
<220> FEATURE:
<221> NAME/KEY: misc_feature
<222> LOCATION: (11)..(11)
<223> OTHER INFORMATION: Xaa can be any kind of amino acid known in the art

<400> SEQUENCE: 10

Lys Lys Arg Tyr Asp Arg Glu Phe Leu Leu Xaa Phe Gln Phe
1               5                   10

<210> SEQ ID NO 11
<211> LENGTH: 15
<212> TYPE: PRT
<213> ORGANISM: Artificial
<220> FEATURE:
<223> OTHER INFORMATION: Designed peptide based on eIF4G1 peptide
<220> FEATURE:
<221> NAME/KEY: misc_feature
<222> LOCATION: (12)..(12)
<223> OTHER INFORMATION: Xaa can be any kind of amino acid known in the art

<400> SEQUENCE: 11

Thr Lys Lys Arg Tyr Asp Arg Glu Phe Leu Leu Xaa Phe Gln Phe
1               5                   10                  15

<210> SEQ ID NO 12
<211> LENGTH: 13
<212> TYPE: PRT
<213> ORGANISM: Artificial
<220> FEATURE:
<223> OTHER INFORMATION: Designed peptide based on eIF4G1 peptide
<220> FEATURE:
<221> NAME/KEY: misc_feature
<222> LOCATION: (10)..(10)
<223> OTHER INFORMATION: Xaa can be any kind of amino acid known in the art

<400> SEQUENCE: 12

Lys Arg Tyr Asp Arg Glu Phe Leu Leu Xaa Phe Gln Phe

<210> SEQ ID NO 13
<211> LENGTH: 12
<212> TYPE: PRT
<213> ORGANISM: Artificial
<220> FEATURE:
<223> OTHER INFORMATION: Designed peptide based on eIF4G1 peptide
<220> FEATURE:
<221> NAME/KEY: misc_feature
<222> LOCATION: (9)..(9)
<223> OTHER INFORMATION: Xaa can be any kind of amino acid known in the art

<400> SEQUENCE: 13

Arg Tyr Asp Arg Glu Phe Leu Leu Xaa Phe Gln Phe
1               5                   10

<210> SEQ ID NO 14
<211> LENGTH: 11
<212> TYPE: PRT
<213> ORGANISM: Artificial
<220> FEATURE:
<223> OTHER INFORMATION: Designed peptide based on eIF4G1 peptide
<220> FEATURE:
<221> NAME/KEY: misc_feature
<222> LOCATION: (8)..(8)
<223> OTHER INFORMATION: Xaa can be any kind of amino acid known in the art

<400> SEQUENCE: 14

Tyr Asp Arg Glu Phe Leu Leu Xaa Phe Gln Phe
1               5                   10

<210> SEQ ID NO 15
<211> LENGTH: 14
<212> TYPE: PRT
<213> ORGANISM: Artificial
<220> FEATURE:
<223> OTHER INFORMATION: Designed peptide based on eIF4G1 peptide

<400> SEQUENCE: 15

Lys Ile Ile Tyr Asp Arg Glu Phe Leu Leu Gly Phe Gln Phe
1               5                   10

<210> SEQ ID NO 16
<211> LENGTH: 14
<212> TYPE: PRT
<213> ORGANISM: Artificial
<220> FEATURE:
<223> OTHER INFORMATION: Designed peptide based on eIF4G1 peptide

<400> SEQUENCE: 16

Lys Lys Arg Tyr Thr Arg Glu Phe Leu Leu Gly Phe Gln Phe
1               5                   10

<210> SEQ ID NO 17
<211> LENGTH: 10
<212> TYPE: PRT
<213> ORGANISM: Artificial
<220> FEATURE:
<223> OTHER INFORMATION: Tr1

<400> SEQUENCE: 17

Lys Lys Arg Tyr Asp Arg Glu Phe Leu Leu
1               5                   10

<210> SEQ ID NO 18

```
<211> LENGTH: 11
<212> TYPE: PRT
<213> ORGANISM: Artificial
<220> FEATURE:
<223> OTHER INFORMATION: Tr2

<400> SEQUENCE: 18

Tyr Asp Arg Glu Phe Leu Leu Gly Phe Gln Phe
1               5                   10

<210> SEQ ID NO 19
<211> LENGTH: 10
<212> TYPE: PRT
<213> ORGANISM: Artificial
<220> FEATURE:
<223> OTHER INFORMATION: Tr3

<400> SEQUENCE: 19

Tyr Asp Arg Glu Phe Leu Leu Gly Phe Gln
1               5                   10

<210> SEQ ID NO 20
<211> LENGTH: 11
<212> TYPE: PRT
<213> ORGANISM: Artificial
<220> FEATURE:
<223> OTHER INFORMATION: Control

<400> SEQUENCE: 20

Ala Asp Arg Glu Phe Leu Leu Gly Phe Gln Phe
1               5                   10

<210> SEQ ID NO 21
<211> LENGTH: 11
<212> TYPE: PRT
<213> ORGANISM: Artificial
<220> FEATURE:
<223> OTHER INFORMATION: Tr2_AIB1
<220> FEATURE:
<221> NAME/KEY: misc_feature
<222> LOCATION: (2)..(2)
<223> OTHER INFORMATION: Xaa is Aib

<400> SEQUENCE: 21

Tyr Xaa Arg Glu Phe Leu Leu Gly Phe Gln Phe
1               5                   10

<210> SEQ ID NO 22
<211> LENGTH: 11
<212> TYPE: PRT
<213> ORGANISM: Artificial
<220> FEATURE:
<223> OTHER INFORMATION: Tr2_AIB2
<220> FEATURE:
<221> NAME/KEY: misc_feature
<222> LOCATION: (4)..(4)
<223> OTHER INFORMATION: Xaa is Aib

<400> SEQUENCE: 22

Tyr Asp Arg Xaa Phe Leu Leu Gly Phe Gln Phe
1               5                   10

<210> SEQ ID NO 23
<211> LENGTH: 11
<212> TYPE: PRT
<213> ORGANISM: Artificial
<220> FEATURE:
<223> OTHER INFORMATION: Tr2_AIB3
<220> FEATURE:
```

```
<221> NAME/KEY: misc_feature
<222> LOCATION: (8)..(8)
<223> OTHER INFORMATION: Xaa is Aib

<400> SEQUENCE: 23

Tyr Asp Arg Glu Phe Leu Leu Xaa Phe Gln Phe
1               5                   10

<210> SEQ ID NO 24
<211> LENGTH: 11
<212> TYPE: PRT
<213> ORGANISM: Artificial
<220> FEATURE:
<223> OTHER INFORMATION: Tr2_AIB4
<220> FEATURE:
<221> NAME/KEY: misc_feature
<222> LOCATION: (10)..(10)
<223> OTHER INFORMATION: Xaa is Aib

<400> SEQUENCE: 24

Tyr Asp Arg Glu Phe Leu Leu Gly Phe Xaa Phe
1               5                   10

<210> SEQ ID NO 25
<211> LENGTH: 11
<212> TYPE: PRT
<213> ORGANISM: Artificial
<220> FEATURE:
<223> OTHER INFORMATION: Tr2_AIB3_ALA

<400> SEQUENCE: 25

Tyr Asp Arg Glu Phe Leu Leu Ala Phe Gln Phe
1               5                   10

<210> SEQ ID NO 26
<211> LENGTH: 11
<212> TYPE: PRT
<213> ORGANISM: Artificial
<220> FEATURE:
<223> OTHER INFORMATION: Tr2_AIB3_A3C
<220> FEATURE:
<221> NAME/KEY: misc_feature
<222> LOCATION: (8)..(8)
<223> OTHER INFORMATION: Xaa is 1-amino cyclopropanoic acid

<400> SEQUENCE: 26

Tyr Asp Arg Glu Phe Leu Leu Xaa Phe Gln Phe
1               5                   10

<210> SEQ ID NO 27
<211> LENGTH: 11
<212> TYPE: PRT
<213> ORGANISM: Artificial
<220> FEATURE:
<223> OTHER INFORMATION: Tr2_AIB3_A4C
<220> FEATURE:
<221> NAME/KEY: misc_feature
<222> LOCATION: (8)..(8)
<223> OTHER INFORMATION: Xaa is 1-amino cyclobutanoic acid

<400> SEQUENCE: 27

Tyr Asp Arg Glu Phe Leu Leu Xaa Phe Gln Phe
1               5                   10

<210> SEQ ID NO 28
<211> LENGTH: 11
<212> TYPE: PRT
<213> ORGANISM: Artificial
<220> FEATURE:
```

-continued

```
<223> OTHER INFORMATION: Tr2_AIB3_A5C
<220> FEATURE:
<221> NAME/KEY: misc_feature
<222> LOCATION: (8)..(8)
<223> OTHER INFORMATION: Xaa is 1-amino cyclopentanoic acid

<400> SEQUENCE: 28

Tyr Asp Arg Glu Phe Leu Leu Xaa Phe Gln Phe
1               5                   10

<210> SEQ ID NO 29
<211> LENGTH: 11
<212> TYPE: PRT
<213> ORGANISM: Artificial
<220> FEATURE:
<223> OTHER INFORMATION: Tr2_ALA_A5C1
<220> FEATURE:
<221> NAME/KEY: misc_feature
<222> LOCATION: (8)..(8)
<223> OTHER INFORMATION: Xaa is 1-amino cyclopentanoic acid

<400> SEQUENCE: 29

Tyr Ala Arg Glu Phe Leu Leu Xaa Phe Gln Phe
1               5                   10

<210> SEQ ID NO 30
<211> LENGTH: 11
<212> TYPE: PRT
<213> ORGANISM: Artificial
<220> FEATURE:
<223> OTHER INFORMATION: Tr2_ALA_A5C2
<220> FEATURE:
<221> NAME/KEY: misc_feature
<222> LOCATION: (8)..(8)
<223> OTHER INFORMATION: Xaa is 1-amino cyclopentanoic acid

<400> SEQUENCE: 30

Tyr Asp Ala Glu Phe Leu Leu Xaa Phe Gln Phe
1               5                   10

<210> SEQ ID NO 31
<211> LENGTH: 11
<212> TYPE: PRT
<213> ORGANISM: Artificial
<220> FEATURE:
<223> OTHER INFORMATION: Tr2_ALA_A5C3
<220> FEATURE:
<221> NAME/KEY: misc_feature
<222> LOCATION: (8)..(8)
<223> OTHER INFORMATION: Xaa is 1-amino cyclopentanoic acid

<400> SEQUENCE: 31

Tyr Asp Arg Ala Phe Leu Leu Xaa Phe Gln Phe
1               5                   10

<210> SEQ ID NO 32
<211> LENGTH: 11
<212> TYPE: PRT
<213> ORGANISM: Artificial
<220> FEATURE:
<223> OTHER INFORMATION: Tr2_ALA_A5C4
<220> FEATURE:
<221> NAME/KEY: misc_feature
<222> LOCATION: (8)..(8)
<223> OTHER INFORMATION: Xaa is 1-amino cyclopentanoic acid

<400> SEQUENCE: 32

Tyr Asp Arg Glu Ala Leu Leu Xaa Phe Gln Phe
1               5                   10
```

<210> SEQ ID NO 33
<211> LENGTH: 11
<212> TYPE: PRT
<213> ORGANISM: Artificial
<220> FEATURE:
<223> OTHER INFORMATION: Tr2_ALA_A5C5
<220> FEATURE:
<221> NAME/KEY: misc_feature
<222> LOCATION: (8)..(8)
<223> OTHER INFORMATION: Xaa is 1-amino cyclopentanoic acid

<400> SEQUENCE: 33

Tyr Asp Arg Glu Phe Leu Leu Xaa Ala Gln Phe
1               5                   10

<210> SEQ ID NO 34
<211> LENGTH: 11
<212> TYPE: PRT
<213> ORGANISM: Artificial
<220> FEATURE:
<223> OTHER INFORMATION: Tr2_ALA_A5C6
<220> FEATURE:
<221> NAME/KEY: misc_feature
<222> LOCATION: (8)..(8)
<223> OTHER INFORMATION: Xaa is 1-amino cyclopentanoic acid

<400> SEQUENCE: 34

Tyr Asp Arg Glu Phe Leu Leu Xaa Phe Ala Phe
1               5                   10

<210> SEQ ID NO 35
<211> LENGTH: 11
<212> TYPE: PRT
<213> ORGANISM: Artificial
<220> FEATURE:
<223> OTHER INFORMATION: Tr2_ALA_A5C7
<220> FEATURE:
<221> NAME/KEY: misc_feature
<222> LOCATION: (8)..(8)
<223> OTHER INFORMATION: Xaa is 1-amino cyclopentanoic acid

<400> SEQUENCE: 35

Tyr Asp Arg Glu Phe Leu Leu Xaa Phe Gln Ala
1               5                   10

<210> SEQ ID NO 36
<211> LENGTH: 11
<212> TYPE: PRT
<213> ORGANISM: Artificial
<220> FEATURE:
<223> OTHER INFORMATION: Tr2_me5_1
<220> FEATURE:
<221> NAME/KEY: misc_feature
<222> LOCATION: (5)..(5)
<223> OTHER INFORMATION: Xaa is Calpha-Me-L-Phenylalanine
<220> FEATURE:
<221> NAME/KEY: misc_feature
<222> LOCATION: (8)..(8)
<223> OTHER INFORMATION: Xaa is 1-amino cyclopentanoic acid

<400> SEQUENCE: 36

Tyr Asp Arg Glu Xaa Leu Leu Xaa Phe Gln Phe
1               5                   10

<210> SEQ ID NO 37
<211> LENGTH: 11
<212> TYPE: PRT
<213> ORGANISM: Artificial
<220> FEATURE:
<223> OTHER INFORMATION: Tr2_me5_2

```
<220> FEATURE:
<221> NAME/KEY: misc_feature
<222> LOCATION: (8)..(8)
<223> OTHER INFORMATION: Xaa is 1-amino cyclopentanoic acid
<220> FEATURE:
<221> NAME/KEY: misc_feature
<222> LOCATION: (9)..(9)
<223> OTHER INFORMATION: Xaa is Calpha-Me-L-Phenylalanine

<400> SEQUENCE: 37

Tyr Asp Arg Glu Phe Leu Leu Xaa Xaa Gln Phe
1               5                   10

<210> SEQ ID NO 38
<211> LENGTH: 11
<212> TYPE: PRT
<213> ORGANISM: Artificial
<220> FEATURE:
<223> OTHER INFORMATION: Tr2_me5_3
<220> FEATURE:
<221> NAME/KEY: misc_feature
<222> LOCATION: (8)..(8)
<223> OTHER INFORMATION: Xaa is 1-amino cyclopentanoic acid
<220> FEATURE:
<221> NAME/KEY: misc_feature
<222> LOCATION: (11)..(11)
<223> OTHER INFORMATION: Xaa is Calpha-Me-L-Phenylalanine

<400> SEQUENCE: 38

Tyr Asp Arg Glu Phe Leu Leu Xaa Phe Gln Xaa
1               5                   10

<210> SEQ ID NO 39
<211> LENGTH: 14
<212> TYPE: PRT
<213> ORGANISM: Artificial
<220> FEATURE:
<223> OTHER INFORMATION: eIF4G1_me5
<220> FEATURE:
<221> NAME/KEY: misc_feature
<222> LOCATION: (8)..(8)
<223> OTHER INFORMATION: Xaa is Calpha-Me-L-Phenylalanine
<220> FEATURE:
<221> NAME/KEY: misc_feature
<222> LOCATION: (11)..(11)
<223> OTHER INFORMATION: Xaa is 1-amino cyclopentanoic acid

<400> SEQUENCE: 39

Lys Lys Arg Tyr Asp Arg Glu Xaa Leu Leu Xaa Phe Gln Phe
1               5                   10

<210> SEQ ID NO 40
<211> LENGTH: 27
<212> TYPE: PRT
<213> ORGANISM: Artificial
<220> FEATURE:
<223> OTHER INFORMATION: TAT_eIF4G1

<400> SEQUENCE: 40

Tyr Gly Arg Lys Lys Arg Arg Gln Arg Arg Gly Thr Lys Lys Arg
1               5                   10                  15

Tyr Asp Arg Glu Phe Leu Leu Gly Phe Gln Phe
            20                  25

<210> SEQ ID NO 41
<211> LENGTH: 27
<212> TYPE: PRT
<213> ORGANISM: Artificial
<220> FEATURE:
<223> OTHER INFORMATION: TAT_eIF4G1_Cntrl
```

<400> SEQUENCE: 41

Tyr Gly Arg Lys Lys Arg Arg Gln Arg Arg Arg Gly Thr Lys Lys Arg
1               5                   10                  15

Ala Asp Arg Glu Phe Ala Ala Gly Phe Gln Phe
            20                  25

<210> SEQ ID NO 42
<211> LENGTH: 27
<212> TYPE: PRT
<213> ORGANISM: Artificial
<220> FEATURE:
<223> OTHER INFORMATION: TAT_eIF4G1_me5
<220> FEATURE:
<221> NAME/KEY: misc_feature
<222> LOCATION: (21)..(21)
<223> OTHER INFORMATION: Xaa is Calpha-Me-L-Phenylalanine
<220> FEATURE:
<221> NAME/KEY: misc_feature
<222> LOCATION: (24)..(24)
<223> OTHER INFORMATION: Xaa is 1-amino cyclopentanoic acid

<400> SEQUENCE: 42

Tyr Gly Arg Lys Lys Arg Arg Gln Arg Arg Arg Gly Thr Lys Lys Arg
1               5                   10                  15

Tyr Asp Arg Glu Xaa Leu Leu Xaa Phe Gln Phe
            20                  25

<210> SEQ ID NO 43
<211> LENGTH: 27
<212> TYPE: PRT
<213> ORGANISM: Artificial
<220> FEATURE:
<223> OTHER INFORMATION: TAT_eIF4G1_me5_Cntrl
<220> FEATURE:
<221> NAME/KEY: misc_feature
<222> LOCATION: (21)..(21)
<223> OTHER INFORMATION: Xaa is Calpha-Me-L-Phenylalanine
<220> FEATURE:
<221> NAME/KEY: misc_feature
<222> LOCATION: (24)..(24)
<223> OTHER INFORMATION: Xaa is 1-amino cyclopentanoic acid

<400> SEQUENCE: 43

Tyr Gly Arg Lys Lys Arg Arg Gln Arg Arg Arg Gly Thr Lys Lys Arg
1               5                   10                  15

Ala Asp Arg Glu Xaa Ala Ala Xaa Phe Gln Phe
            20                  25

<210> SEQ ID NO 44
<211> LENGTH: 16
<212> TYPE: PRT
<213> ORGANISM: Artificial
<220> FEATURE:
<223> OTHER INFORMATION: GT_eIF4G1

<400> SEQUENCE: 44

Gly Thr Lys Lys Arg Tyr Asp Arg Glu Phe Leu Leu Gly Phe Gln Phe
1               5                   10                  15

<210> SEQ ID NO 45
<211> LENGTH: 16
<212> TYPE: PRT
<213> ORGANISM: Artificial
<220> FEATURE:
<223> OTHER INFORMATION: GT_eIF4G1_Cntrl

<400> SEQUENCE: 45

Gly Thr Lys Lys Arg Ala Asp Arg Glu Phe Ala Ala Gly Phe Gln Phe
1               5                   10                  15

<210> SEQ ID NO 46
<211> LENGTH: 16
<212> TYPE: PRT
<213> ORGANISM: Artificial
<220> FEATURE:
<223> OTHER INFORMATION: GT_eIF4G1_me5
<220> FEATURE:
<221> NAME/KEY: misc_feature
<222> LOCATION: (10)..(10)
<223> OTHER INFORMATION: Xaa is Calpha-Me-L-Phenylalanine
<220> FEATURE:
<221> NAME/KEY: misc_feature
<222> LOCATION: (13)..(13)
<223> OTHER INFORMATION: Xaa is 1-amino cyclopentanoic acid

<400> SEQUENCE: 46

Gly Thr Lys Lys Arg Tyr Asp Arg Glu Xaa Leu Leu Xaa Phe Gln Phe
1               5                   10                  15

<210> SEQ ID NO 47
<211> LENGTH: 16
<212> TYPE: PRT
<213> ORGANISM: Artificial
<220> FEATURE:
<223> OTHER INFORMATION: GT_eIF4G1_me5_Cntrl
<220> FEATURE:
<221> NAME/KEY: misc_feature
<222> LOCATION: (10)..(10)
<223> OTHER INFORMATION: Xaa is Calpha-Me-L-Phenylalanine
<220> FEATURE:
<221> NAME/KEY: misc_feature
<222> LOCATION: (13)..(13)
<223> OTHER INFORMATION: Xaa is 1-amino cyclopentanoic acid

<400> SEQUENCE: 47

Gly Thr Lys Lys Arg Ala Asp Arg Glu Xaa Ala Ala Xaa Phe Gln Phe
1               5                   10                  15

<210> SEQ ID NO 48
<211> LENGTH: 15
<212> TYPE: PRT
<213> ORGANISM: Artificial
<220> FEATURE:
<223> OTHER INFORMATION: Ac15
<220> FEATURE:
<221> NAME/KEY: misc_feature
<222> LOCATION: (9)..(9)
<223> OTHER INFORMATION: Xaa is Calpha-Me-L-Phenylalanine
<220> FEATURE:
<221> NAME/KEY: misc_feature
<222> LOCATION: (12)..(12)
<223> OTHER INFORMATION: Xaa is 1-amino cyclopentanoic acid

<400> SEQUENCE: 48

Thr Lys Lys Arg Tyr Asp Arg Glu Xaa Leu Leu Xaa Phe Gln Phe
1               5                   10                  15

<210> SEQ ID NO 49
<211> LENGTH: 13
<212> TYPE: PRT
<213> ORGANISM: Artificial
<220> FEATURE:
<223> OTHER INFORMATION: Ac13
<220> FEATURE:
<221> NAME/KEY: misc_feature
<222> LOCATION: (7)..(7)
<223> OTHER INFORMATION: Xaa is Calpha-Me-L-Phenylalanine
<220> FEATURE:

```
<221> NAME/KEY: misc_feature
<222> LOCATION: (10)..(10)
<223> OTHER INFORMATION: Xaa is 1-amino cyclopentanoic acid

<400> SEQUENCE: 49

Lys Arg Tyr Asp Arg Glu Xaa Leu Leu Xaa Phe Gln Phe
1               5                   10

<210> SEQ ID NO 50
<211> LENGTH: 12
<212> TYPE: PRT
<213> ORGANISM: Artificial
<220> FEATURE:
<223> OTHER INFORMATION: Ac12
<220> FEATURE:
<221> NAME/KEY: misc_feature
<222> LOCATION: (6)..(6)
<223> OTHER INFORMATION: Xaa is Calpha-Me-L-Phenylalanine
<220> FEATURE:
<221> NAME/KEY: misc_feature
<222> LOCATION: (9)..(9)
<223> OTHER INFORMATION: Xaa is 1-amino cyclopentanoic acid

<400> SEQUENCE: 50

Arg Tyr Asp Arg Glu Xaa Leu Leu Xaa Phe Gln Phe
1               5                   10

<210> SEQ ID NO 51
<211> LENGTH: 11
<212> TYPE: PRT
<213> ORGANISM: Artificial
<220> FEATURE:
<223> OTHER INFORMATION: Ac11
<220> FEATURE:
<221> NAME/KEY: misc_feature
<222> LOCATION: (5)..(5)
<223> OTHER INFORMATION: Xaa is Calpha-Me-L-Phenylalanine
<220> FEATURE:
<221> NAME/KEY: misc_feature
<222> LOCATION: (8)..(8)
<223> OTHER INFORMATION: Xaa is 1-amino cyclopentanoic acid

<400> SEQUENCE: 51

Tyr Asp Arg Glu Xaa Leu Leu Xaa Phe Gln Phe
1               5                   10
```